US007744819B2

(12) United States Patent
Berndtsson et al.

(10) Patent No.: US 7,744,819 B2
(45) Date of Patent: Jun. 29, 2010

(54) APPARATUS FOR FILLING A SAMPLE VOLUME DEFINING DEVICE

(75) Inventors: Ingemar Berndtsson, Sollentuna (SE); Lennart Niklason, Sollentuna (SE)

(73) Assignee: Boule Medical AB, Stockholm (SE)

( * ) Notice: Subject to any disclaimer, the term of this patent is extended or adjusted under 35 U.S.C. 154(b) by 758 days.

(21) Appl. No.: 11/399,423

(22) Filed: Apr. 7, 2006

(65) Prior Publication Data
US 2006/0228263 A1    Oct. 12, 2006

(30) Foreign Application Priority Data
Apr. 8, 2005   (SE) .................................. 0500784

(51) Int. Cl.
*B01L 3/00*   (2006.01)
*G01N 1/18*   (2006.01)

(52) U.S. Cl. .................. 422/100; 73/863; 222/335; 222/399; 422/93; 422/103; 436/177; 436/180

(58) Field of Classification Search .................. 422/100
See application file for complete search history.

(56) References Cited

U.S. PATENT DOCUMENTS

| | | | | |
|---|---|---|---|---|
| 4,726,237 A | * | 2/1988 | Yung | ........................ 73/864.83 |
| 4,726,932 A | * | 2/1988 | Feier et al. | .................... 422/103 |
| 4,896,546 A | * | 1/1990 | Cabrera et al. | ............ 73/863.73 |
| 5,637,469 A | * | 6/1997 | Wilding et al. | .............. 435/7.21 |
| 6,240,984 B1 | * | 6/2001 | Fawcett et al. | ............... 141/130 |
| 6,872,361 B2 | * | 3/2005 | Li et al. | ........................ 422/103 |
| 2002/0172617 A1 | | 11/2002 | Biwa et al. | |
| 2003/0026741 A1 | | 2/2003 | Li et al. | |
| 2003/0099577 A1 | * | 5/2003 | Renaud et al. | ............... 422/100 |
| 2005/0118061 A1 | | 6/2005 | Mototsu | |

FOREIGN PATENT DOCUMENTS

WO   WO-2005/052553 A1   6/2005

* cited by examiner

*Primary Examiner*—Krishnan S Menon
*Assistant Examiner*—Dirk Bass
(74) *Attorney, Agent, or Firm*—Latimer IP Law, LLP

(57) ABSTRACT

An apparatus for filling a sample volume defining device for separating at least one small defined volume of a liquid sample from a relatively larger undefined volume of said sample, said device including a first body and a second body movable relative to each other, whereby said first body has at least one cavity in a surface thereof, said at least one cavity having said defined volume. One of said first or said second body has at least one inlet opening adapted to be placed in a drop of the liquid sample. A defined channel is provided between said first and second body, which channel has fluid connection with said at least one opening and at least beyond said at least one cavity whereby the dimensions of said channel being such that said channel and said at least one cavity is filled with said liquid sample.

19 Claims, 8 Drawing Sheets

A - A

B - B

APPARATUS FOR FILLING A SAMPLE VOLUME DEFINING DEVICE

FIELD OF THE INVENTION

The present invention relates an apparatus for filling a sample volume defining device, particularly a disposable sample volume defining device, for separating at least one small defined volume of a liquid sample from a relatively larger undefined volume of said sample, said device including a first body and a second body movable relative to each other, whereby said first body has at least one cavity in a surface thereof, said at least one cavity having said defined volume, and said second body includes a means slidable along said surface and over said at least one cavity upon relative movement of said bodies, whereby said defined volume is achieved in said at least one cavity. The liquid sample is a blood sample, for instance.

BACKGROUND OF THE INVENTION

In blood testing, it is of crucial importance to define an accurate volume of a blood sample, since such accurately defined volume is later on used for certain tests. The accurately defined volume of blood sample is normally diluted by an accurately defined volume of a diluent or a lysing agent, in order to obtain a dilution of typically 1:100 to 1:80000. When counting white blood cells is concerned the dilution is typically 1:400 and when counting red blood cells (RBC) is concerned the dilution is typically 1:40000, in the latter case the dilution normally taking place in two steps. It is obvious, that measurement of sample volumes and dilution liquid volumes must be performed in an accurate and repeatable way such that a correct degree of dilution can always be guaranteed. Apparently, accurate measurement of sample volumes is a critical step in the dilution procedure, since the volumes concerned are extremely small compared to the corresponding diluent volumes.

To be able to obtain an accurate volume of a blood sample it is of crucial importance that the means in which the blood sample is contained is filled in a very precise and accurate and repeatable way.

A sample volume defining device of the above-identified type is known from the co-pending Swedish Patent Application No. 0303157-2. It has usually the form of a disposable cassette.

One problem when filling small cavities or voids or the like for obtaining the accurate and repeatable volume of a liquid sample, preferably a blood sample, is that the cavities are not filled in a proper way due to the formation of air bubbles in the cavities designed for the blood sample. Thus, there will be a difference in the volume between different blood samples and this will have a large significance when later counting the blood cells.

Another problem with known apparatus for testing of small volumes of a liquid sample/blood sample is to see when the apparatus is correctly filled.

Another problem is that the filling of known apparatus for testing of small volumes of a liquid sample/blood is dependent upon the direction of the apparatus when it is filled.

SUMMARY OF THE INVENTION

The object of present invention is to providing an apparatus for filling a sample volume defining device comprising at least two relatively movable bodies, one of which is provided with at least one cavity to be filled with liquid sample, for separating at least one accurately defined volume of a liquid sample from a relatively larger undefined volume of said sample.

A further object is to provide an apparatus of the above type in which it is easy to see when the cavity is filled with the liquid sample in an accurate and repeatable way.

A further object is to achieve an apparatus of the above type which is not dependent upon the filling direction.

Said object is achieved according to the present invention by an apparatus which is characterized in that that one of said first or said second body has at least one inlet opening adapted to be connected with a drop of the liquid sample, that a defined channel is provided between said first and second body, which channel has fluid connection with said at least one inlet opening and at least beyond said at least one cavity, and that the dimensions of said channel being such that said channel and thereby said at least one cavity is filled with said liquid by capillary force.

As indicated a sample volume defining device is known from the co-pending application SE 0303157-2, incorporated by reference herein. Basically the volume defining process incorporates a) application of a relatively larger, often undefined, volume of the sample onto a surface and into a cavity formed in the surface and b) moving a scraping edge over the surface to leave a smaller defined volume of the sample in, the cavity. Further processing steps may follow, such as c) flushing the cavity with a liquid, such as a solution or reagent, to obtain a diluted sample, d) mixing the sample and diluent to obtain a homogenous diluted sample and e) performing measurements on the diluted and mixed sample.

For purposes of discussion the surface can be regarded as a reference surface, comprising the physical surface as well as an imaginary surface, flush and continuous with the physical surface, or defined in mechanical terms by movement of a thought entirely rigid scraper means in contact with the surface, across the cavity so as to define a target volume of the cavity limited by the imaginary surface. The reference surface shall at least surround the cavity to such an extent as to allow the scraping action and preferably the reference surface encircles the cavity on all sides.

The reference surface may have different shapes as long as it meets the continuity requirement, consistent with the scraping purpose. For example, the reference surface with its cavity may be double-curved, meaning that it cannot be formed by bending a flat surface, as exemplified with a cavity in a ball valve, or the reference surface may preferably be single-curved, meaning that it can be formed from a flat surface, as exemplified by a cavity in a cylinder valve, or most preferably it is substantially flat, as exemplified by a cavity in a slide valve.

The cavity size, i.e. the target volume under the imaginary surface, or rather the practical surface to be further discussed below, depends on several factors. Some of these factors are application dependent, such as sample nature and necessary volumes for planned dilution degrees or requirements for intended measurement. In disposable devices, for economical, reasons it is generally desirable to minimize the volumes in order also to minimize other features such as diluent volumes, mixing arrangements etc. However, manual manipulation and manufacturing constraints, e.g. molding of plastics, may place a lower limit to practical or possible cavity sizes. In case of several cavities, e.g. for different dilution degrees, the restrictions typically are set by the smallest cavity. General values are difficult to give but experience has indicated that the cavity volume should preferably be larger than 0.01 µl, preferably larger than 0.05 and most preferable larger than 0.1

μl. The maximum cavity volume can be kept below 50 μl, preferably below 25 μl and most preferably below 15 μl.

Similarly cavity shape may be determined by several factors. Besides manufacturing constraints that may put limits to advanced features of small cavities, desirable shape is mainly dictated by efficient filling and foreseeable, also expressed herein as reproducible, scraping results, of particular importance between different disposable devices.

Cavity filling may take place in various ways. As indicated, if a sample surplus is simply placed on the cavity there is a risk for gas inclusion and unfilled voids in the cavity. To avoid this the sample may be forced into the cavity, e.g. by a sample stream positively pumped by forced flow past the cavity, which, however, does not entirely secures flow through the cavity. Preferably then forced filling is made by insertion of a probe straight above or into the cavity, preferably with care taken against probe outlet contact and blocking, which cannot easily be compensated by increased injection pressure due to the hydraulic area relationship, and with necessary precision care needed for small cavities.

A preferred filling method is use of capillary forces for filling. It is believed that such filling takes place by wetting of liquid attraction surfaces highly independent of other forces applied to the liquid sample. Hence the criteria for capillary filling shall be regarded satisfied, and accordingly testable, if filling takes place, or can take place, without other forces applied. The criteria for filling without other forces applied is testable also in devices designed for application with other forces, e.g. syringe or gravity filling of sample into a channel designed for capillary filling. The non-presence of additional forces shall exclude forces needed to initiate capillary filling, which may require forced introduction of the liquid into a channel designed for capillary filling, e.g. forced wetting of a certain part of channel circumference for the capillary filling to continue autonomously. Capillary filling requires a certain surface to volume ratio to proceed, which ratio depends mainly on dimensions but also on among others on liquid to surface wetting attraction, the surface possibly being material selected or modified by plasma treatment, chemical modification, surface treatment etc., normally requiring a certain circumference length in relation to cross-section, which circumference need not be continuous but preferably forms a substantially closed channel. Capillary filling requirements are given by example herein, which requirements, however, should be determined for the actual materials and liquids involved.

Initiation of filling can be made in different ways. The supply can be made substantially along the reference surface, giving advantages in capillary wetting proceeding in the same direction as feeding. The supply can preferably be made from below, i.e. through the same structure that carries the cavity or cavities and with a flow substantially opposite to that needed for filling the cavity, e.g. for the purpose of avoiding interference with the structures introduced to stop capillary filling spreading laterally in the channel. The supply can most preferably be made from above the reference surface, e.g. for the purpose of the above proposes, for gravity assistance, for simplicity in the design and for the possibility of closing the feeding opening during the scraping arrangement movement.

The sample introduction site is preferably designed to assist in the above objects. Preferably the site is designed for compatibility with both direct sample introduction, e.g. a blood drop applied to the site, or device introduction for example by means of a syringe, a probe etc. A preferred design is a funnel ending in the capillary channel, preferably arranged for stopping devices against too deep penetration for reasons given, and most preferably having a narrowest flow area preferably being larger than that required for capillary feeding, thereby assisting in gravity filling, preferably, however, being noncircular, preferably slit-formed, for proper transition between non-capillary and capillary flow. For similar reasons the funnel preferably has a diverging portion after its narrowest part, giving an overall shape of an hour-glass, with a diverging outlet angle adapted for capillary flow for proceeding.

Common in the art are capillary tubes for aspiration of samples. The current cavities differs from such tubes in that the cavities extend from a reference surface, which reference surface in itself forms part of a sample filling channel in general, but preferably a filling channel designed for capillary filling, preferably lateral to cavity filling flow direction. The volume and shape of the filling channel are irrelevant as long as the cavity volume is well defined. The filling channel may comprise several cavities without major modifications of the reference surface carrying device. Filling of cavities arranged remote from, or at least not directly under, channel feeding structures avoids interference with any possible channel feeding device or probe as well as possible later flushing. Simplicity adds advantages over known valve type arrangements.

Without being bound by theory it is believed that capillary filling is driven by liquid affinity to surface and accordingly filling by this mechanism should be facilitated in general terms by a large surface to volume ratio. For a suitable capillary filling design, cavity size and shape come into play. Spherical shapes have the least surface to volume ratio. On the other hand small cavities generally have a larger surface to volume ratio than larger cavities, representing a further argument for minimization, a further merit of the present invention to have realized. Accordingly shape is less important for small cavities where even forms close to spherical or partially spherical can be accepted, whereas larger cavities with preference are given a shape with higher than, partial or full, spherical surface to volume ratio, e.g. tube or channel forms. The distinction between "smaller" and "larger" respectively can herein roughly be understood as cavities having depths "shallower" and "deeper" respectively than double the minimum required for capillary flow to proceed in a continuous channel of that dimension. The reason the cavities can be deeper than the capillary minimum is believed to be that the channel, of capillary dimensions, provides a river of liquid drag that locally, i.e. at the cavities, can overwhelm larger dimensions locally.

Due to the surface wetting theory, it is further believed that sharp edges are easily traversed by a capillary driven liquid front if the edge is concave, i.e. a surface angle in the intersection of less than 180°, as seen from the wet side, whereas convex edges, i.e. a surface angle in the intersection of more than 180°, are less easily traversed. Accordingly it is preferred that that at least the convex edges are smoothed out to facilitate capillary flow transfer by reducing the angle. This preferably applies to the arrival direction of the capillary flow front, i.e. the up-flow end, whereas the other end, i.e. down-flow end, is regarded less critical.

In summary, at least larger cavities should be designed for facilitated capillary filling. Smaller cavities are less critical and, furthermore, common manufacturing methods such as plastic moulding normally result in smoothed out transition surfaces, beneficial for capillary filling. At least the larger cavities are preferably shaped elongated, i.e. having an imaginary surface with a longer axis and a shorter axis perpendicular thereto, which gives an increased circumference to area ratio in relation to a circle, which elongated shape can take a variety of forms such as elliptical, rectangular etc. In case of more complicated forms these can be compared with elliptical shape of the same area for determination of the longer and shorter axes. Preferably such a cavity is located with at least a vector component and preferably its full long axis parallel with the capillary filling flow direction, i.e. with respect to the arriving capillary liquid front, herein referred to as the up-flow direction. The elongated form secures that the cavity has an increase surface to volume ratio in relation to the minimal possible. It is further preferred that the cavity up-flow end has a slow descending slope down into the cavity, as seen in the liquid flow direction, and furthermore that the cavity sides substantially parallel to the flow direction are steep with respect to the reference surface.

The cavity may have several openings, or entrances, e.g. the cavity may form a tube extending between two openings as in known capillary tubes although here also connecting to a capillary driven filling channel. It is preferred, however, that to the extent the channel has more than one opening these opens into one and the same reference surface. Most preferably the cavity has only one opening for best filling and scraping properties.

A sloping arrangement is consistent with a cavity design narrowing away from the reference surface and, in case of cavities with only one opening, towards its bottom or, differently expressed, that cross-sections taken parallel with the reference surface have decreasing cavity areas when moving away from the reference surface, at least over a part of the cavity depth and preferably over substantially the cavity full depth. It is further preferred that the cavity walls are at least substantially perpendicular but preferably converging towards the cavity bottom, the bottom being the end farthest away form the reference surface. Most preferably small or no undercut parts are present in the cavity.

Filling of the cavity or cavities is facilitated if the cavity is designed assist in capillary filling, meaning that cavity surface to volume ratio, at least in the sample flow direction, meets the capillary filling requirement. If the channel has sufficiently strong surface affinity the cavity surfaces may exceed the surface to volume relationship for capillary filling but preferably the cavity dimensions lies within that of the capillary filling requirements, disregarding here the additional dimensions provided by the channel.

Discussing next the scraping, the imaginary surface has been described above as an idealized surface entirely continuous with the reference surface. However, in practice any scraping device able to be kept in good contact with the reference surface must have a certain resilience, preferably the minimum resilience necessary for dynamic adaptation to the reference surface, which is preferably made of a harder material, without undue further deformation. Certainly the material in the scraping device should not be soft, in the sense that it easily deforms permanently. Suitable materials may include thermoplastics and preferably eleastomerics. The scraper resilience means that it will expand by deflection to a certain extent into the cavity volume, thereby creating an actual, or practical, opening surface for the cavity, generally so as to reduce the cavity volume somewhat. This may not be a problem as long as the reduction is predictable and foreseeable. In order to facilitate such predictability it may be of interest to minimize the volume deviation between the imaginary and practical surfaces.

Although the scraping device can expand into the cavity both in the scraping direction and in directions perpendicular thereto, if it in the preferred way has a sufficient length in the scraping direction for coverage of the entire cavity, it is believed that the deviation is reduced if it is elongated as described, i.e. with a shorter axis as well as a longer axis.

In at least on one sense scraping is asymmetrical, namely when the scraping edge enters over the cavity opening, where deflection starts, and even more when the edge leaves the cavity opening, where full deflection must decrease, the latter being deemed more important than the former. In order to minimize influence of at least the latter effect it is preferred to reduce cavity opening size lateral to the scraping direction in relation to the opening size parallel to the scraping direction, consistent with an elongated form as discussed. It is further preferred to avoid linear contact between the scraper edge and at least the cavity edge when entering or at least when leaving the cavity opening, meaning that point contact is preferred during at least leaving. This can be achieved by making the scraping edge non-congruent with the cavity opening leaving edge, e.g. by having a linear scraping edge and a bent cavity opening leaving edge or vice versa, in the latter case preferably by a concave scraping edge in order to lift the peripheral scraping edges prior to lifting its central parts when passing the cavity opening leaving edge. Alternatively the scraper edge can meet an elongated cavity opening at an angle with respect to cavity opening longer axis.

In summary, in order to strike a balance between the cavity shape design dictated by filling and the design dictated by scraping, it is preferred that the cavity has an elongated opening surface and that the filling direction and the scraping direction have at least a vector component in common, preferably a longer vector component in common and most preferably are substantially parallel. It is further preferred that at least the up-flow, and scraping entrance, cavity end wall has a slow slope whereas other cavity wall are steeper.

As indicated, all these observations applies more to larger cavities than to smaller cavities.

BRIEF DESCRIPTION OF THE INVENTION

A non-limiting example of the present inventions will be described hereinafter with reference to the accompanying drawings, wherein.

DESCRIPTION OF PREFERRED EMBODIMENTS

Figure 1:
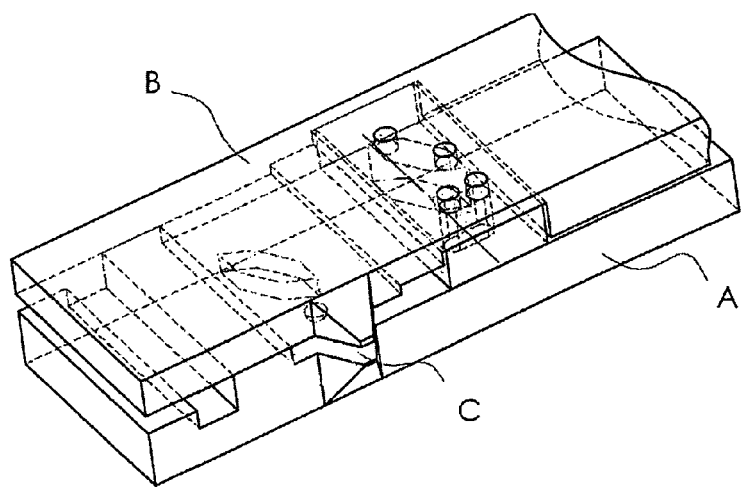
FIG. 1 is a schematic partial perspective view showing the apparatus according to a first embodiment of the invention in which hidden parts and two cavities are shown in phantom lines.

In FIG. 1 the apparatus according to a first embodiment comprises two bodies, i.e. a first body comprising a sledge A and a second body comprising a framework B, movable relatively to each other and in close contact. The apparatus forms a part of a disposable support (not shown), preferably in the form of a cassette, and the framework B is formed integrally with said support. The support comprises at least two chambers, one of which is filled with an accurately defined volume of diluent or lysing agent for dilution of a liquid sample, preferably a blood sample, and the other is used for achieving the dilution and mixing of the liquid sample.

The sledge A or the framework B or both are provided with suitable interengaging means (not shown) so that they can move relative to each other in close contact.

Figure 2:
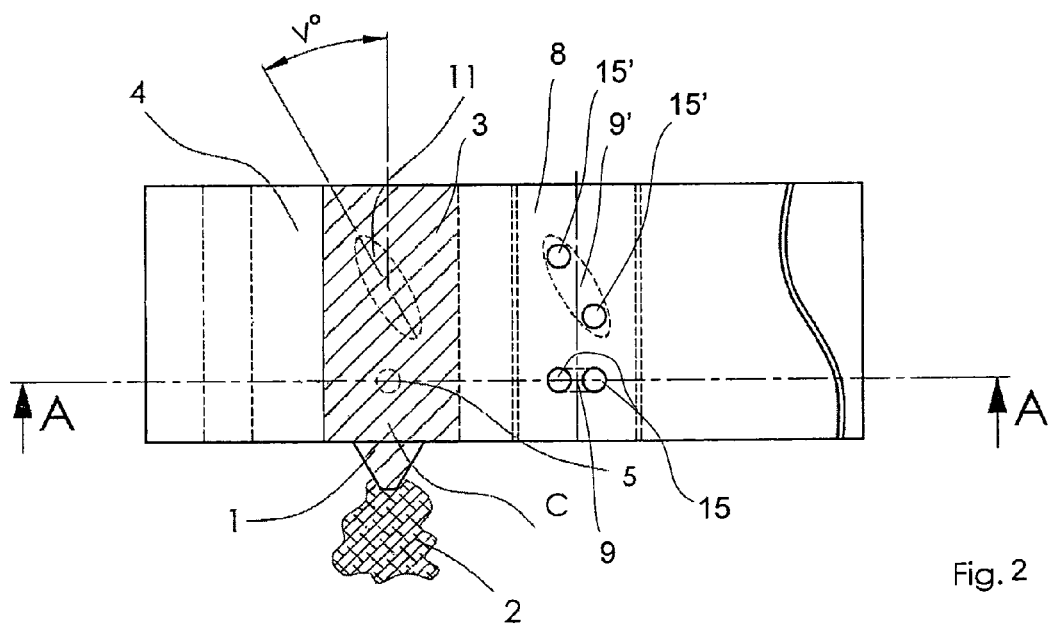
FIG. 2 is a partial view from above of the apparatus according to a first embodiment shown in FIG. 1 in which hidden parts and two cavities are shown in phantom lines, together with a liquid sample to be tested.
Figure 3:
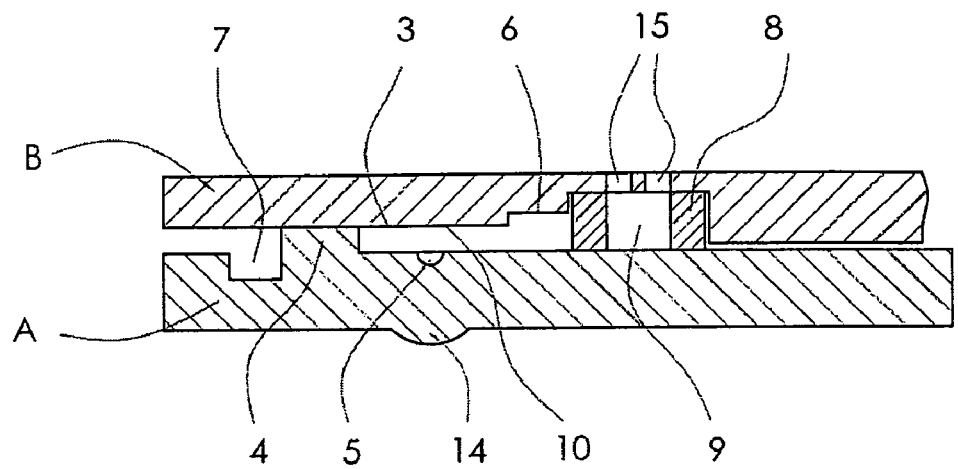
FIG. 3 is a partial sectional side view of the apparatus according to a first embodiment take along the line A-A in FIG. 2.

As can be seen from FIG. 3, between the sledge A and the framework B is a defined channel 3 arranged and provided with at least one inlet opening C for a liquid sample 2 (FIG. 2). To facilitate the filling of the channel the inlet opening C has in a preferred embodiment a protrusion 1.

The channel 3 has fluid connection with and extends as an elongation of said at least one inlet opening and beyond at least one accurately defined cavity 5. The accurately defined cavity 5 is made in the sledge A and aligned with said channel 3.

One aspect of the invention is to fill said at least one cavity 5 with the blood sample in an accurate and repeatable way. The inventors have found this is best done by capillary force. While not wishing to be bounded by a particular theory, the inventors believe that, by using capillary force, the liquid sample forms a wave front in the channel which fills said defined channel 3 and said at least one cavity 5 in such a way that no air bubbles are entrapped in the cavity 5.

By using capillary force for filling, a further aspect of the invention is achieved in that the accurate filling of said at least one cavity 5 is made independent of the direction for filling the apparatus of the disposable support, whereby the disposable support can be handled in a much easier way by, for instance, a nurse.

For enabling capillary force to be developed, the defined channel, formed in either the sledge A or the framework B or between the sledge and the framework, has a particularly chosen form, and the distance between the framework and the sledge, i.e. the height of the channel, is between 0.05-1.0 mm, preferably 0.1-0.3 mm, and most preferably 0.2 mm.

Below is given an example of how the defined channel can be designed, but the invention should not be regarded as limited to said design. Instead, the inventive conception is that the defined channel is filled with the liquid sample by capillary force.

In the embodiment shown in the FIGS. 1 and 2 two accurately defined cavities 5, 11 are formed in the sledge. As an example the larger cavity 11 has a volume of about 5 µl and the smaller cavity 5 about 0.1 µl, and the volume of the channel 3 is about 20-40 µl. However, to simplify the description of the invention said cavities are described as at least one cavity 5,11.

Thus, according to one aspect of the invention the defined channel 3 has the shape of a rectangle in cross section and is formed between the sledge A and the framework B, and one of the long sides of the channel 3 is delimited by a rim 4 formed on the sledge A and the other long side by a recess 6 formed in the framework B. One of the short sides of the channel 3 forms the inlet opening C and the other short side is open to the ambient air.

The rim 4 has close contact with the framework B, and on the long side of the rim opposite to the channel 3 (to the left as seen in FIG. 3) a recess 7 is arranged which stops the liquid sample from further spreading due to the fact that the distance between the sledge and the framework is too large for a capillary force to be developed. In a similar way, the recess 6 also stops the liquid sample from further spreading. Thus, only the channel will be filled with the liquid sample and this is shown in FIG. 2 with dashed lines. However, the physical means that delimit the channel 3 and recess 6 to the right side, as seen in FIG. 3, is a sealing and scraper means 8.

In principle, the design of the defined channel 3 can be made in many ways but according to the invention, it is important that the capillary force is stopped by some type of barrier means so that only the defined channel is filled with the liquid sample.

The sledge A is preferably made of a transparent material so that it is easily seen when the channel and thereby said at least one cavity 5,11 is accurately filled with the liquid sample, and in the case of a blood sample the defined channel will be seen red.

To further increase the control that said at least one cavity 5,11 is accurately filled with the liquid sample the sledge A may be provided with a magnifying means 14, for instance a magnifying glass, which is made in front of said at least one cavity 5,11, as seen in FIG. 3.

As seen in FIG. 3, for instance, the framework B is provided also with the sealing and scraper means 8 made of nitrile rubber. The sealing and scraper means 8 has at least one aperture 9 or 9' aligned with channels 15 or 15' provided in the framework B and in fluid communication with the at least two chambers in the support (not shown).

Figure 4:
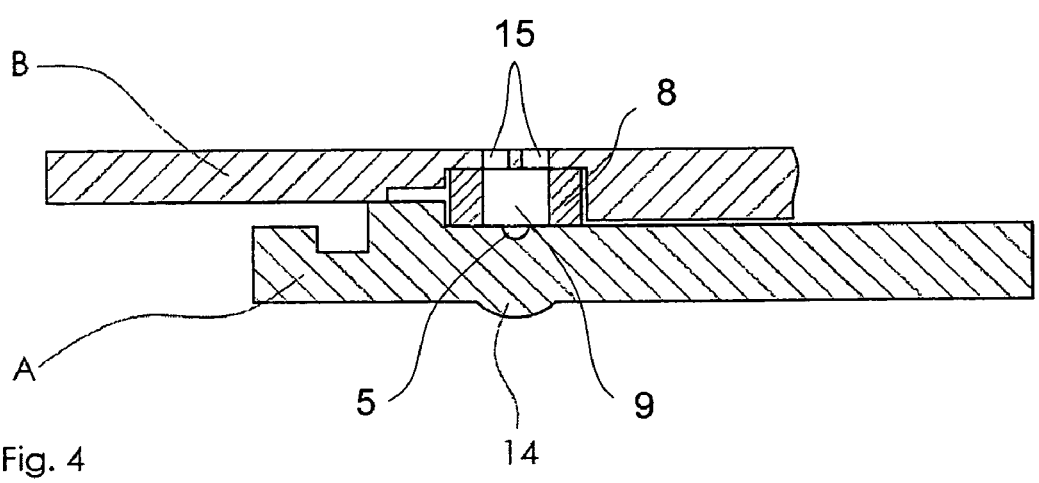
FIG. 4 is a partial sectional side view of the apparatus according to a first embodiment taken along the line A-A in FIG. 2 with the two bodies A, B moved relatively to each other.

In case of blood testing, the channel 3 is filled with blood by capillary force and when the accurately defined volume of blood is to be achieved and diluted by the accurately defined volume of diluent or lysing agent, the sledge A is moved relative to the framework B, as seen in FIG. 4, so that the sealing and scraper means 8 scrapes off the excess of blood in the channel 3, whereby an accurately defined volume of blood is attained in said at least one cavity 5,11. When the sledge A and the framework are moved relative to each other the rim 4 acts as a pusher means for the blood in the channel 3 so that, under no circumstances, the volume of the blood sample in cavities 5,11 will be changed. Said at least one cavity 5,11 is brought also in fluid communication with the channels 15, 15', respectively through the aperture 9, 9', respectively, in the sealing and scraper means 8 and thus the diluent or lysing agent containing chambers. The accurately defined volume of blood is then mixed with the accurately defined volume of diluent or lysing agent and thereafter the blood cells are counted.

In a first embodiment according to the invention said at least one cavity 11 has the shape of an elliptical cavity, as seen from above in FIG. 2, and the major axis of the elliptical cavity preferably makes an angle V with the longitudinal direction of the channel 3 of about 20-60°. The object of arranging the cavity 11 with said angle is to minimize the risk that, when the sledge A and thereby the cavity 11 is moved relative the framework B, the leading edge of the sealing and scraper means 8, which moves over the cavity, expand into the cavity due to the fact that said means is made of a resilient material. If this happens the accurately defined volume of the liquid sample in the cavity will change in an unfavourable way. The cavity 11 having a relatively large volume (about 5 µl) and the cavity 5 having a relatively smaller volume (about 0.1 µl) are filled by the wave front of the liquid sample filling the channel 3 without any air bubbles being formed in said cavities. The smaller cavity 5 can have the form of a half-sphere.

The filling of channel 3 with the liquid sample can be improved if the surfaces enclosing said channel are made of or coated with a material selected from the group consisting of dextran, proteins or derivatives thereof or other means or materials known by the artisan that give a contact angle of 75°-0°, preferably 50°-0°, between the blood and the material forming the surfaces. It may be enough that only the surface of said at least one cavity 5,11 is coated with the above-mentioned material.

Figure 5:
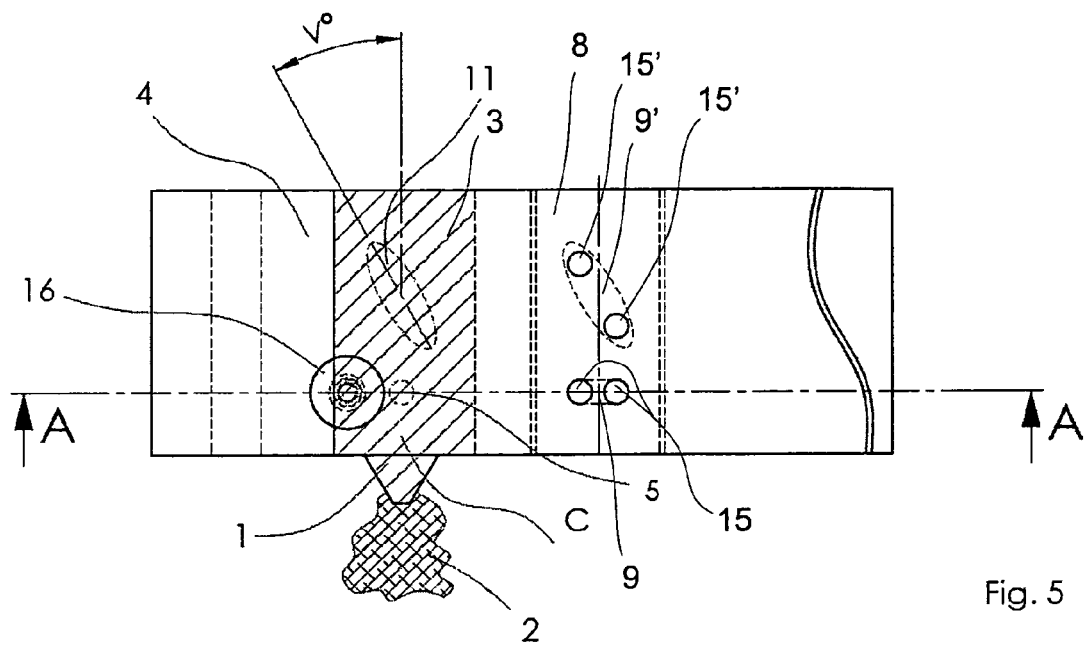
FIG. 5 is a partial view from above of the apparatus according to a second embodiment provided with an syringe inlet through bore and in which hidden parts and two cavities are shown in phantom lines, together with a liquid sample to be tested.
Figure 6:
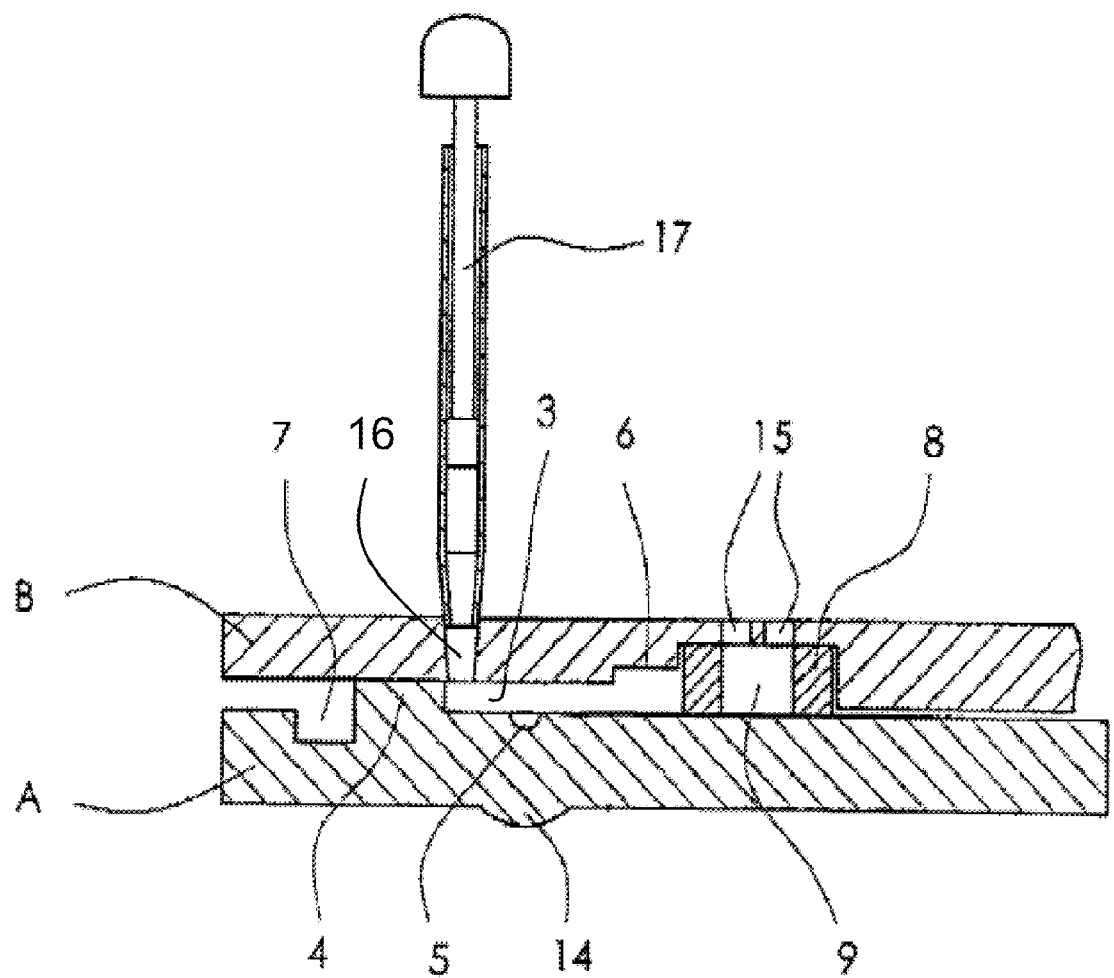
FIG. 6 is a partial sectional side view of the apparatus according to a second embodiment taken along the line A-A in FIG. 5 provided with a syringe.

In FIGS. 5 and 6 a second embodiment of the apparatus according to the invention is shown. The first and the second embodiments of the apparatus according to the invention are made and work in exactly the same way with the exception of that, in the second embodiment, one of the sledge A or the framework B, preferably the framework B, is provided with a syringe inlet through bore 16 which opens in the channel 3, preferably close to rim 4 (see FIG. 6), and in which a syringe 17, preferably a capillary dispenser commercially available from Drummond Scientific Co., the United States, is adapted to be inserted. The channel 3 is thus filled with the liquid sample by a combination of capillary force and injection when said sample is injected and thereby the cavity 5,11 is filled. Thus, the at least one cavity 5,11 is filled in an accurate and repeatable way as in the first embodiment.

Preferably, the volume of the syringe is adapted to the volume of the channel 3 so that the channel 3 is not filled too much when the liquid sample is injected, whereby losses of liquid sample can be avoided.

An advantage when using a syringe for filling the channel 3 is that the liquid sample to be tested can be drawn from a test tube or from any other means, especially in veterinary applications.

Figure 5A:
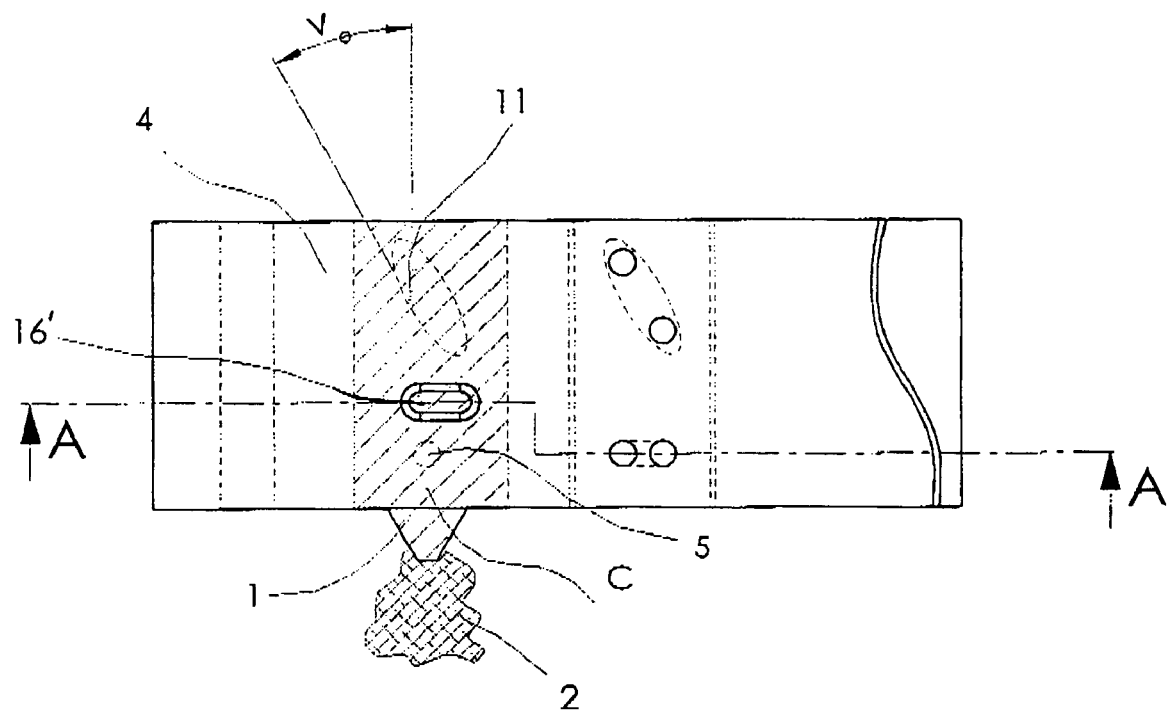
FIGS. 5A and 6A depict a slight modification of the embodiment of FIGS. 5 and 6 in respect of bore 16' form and position.
Figure 6A:
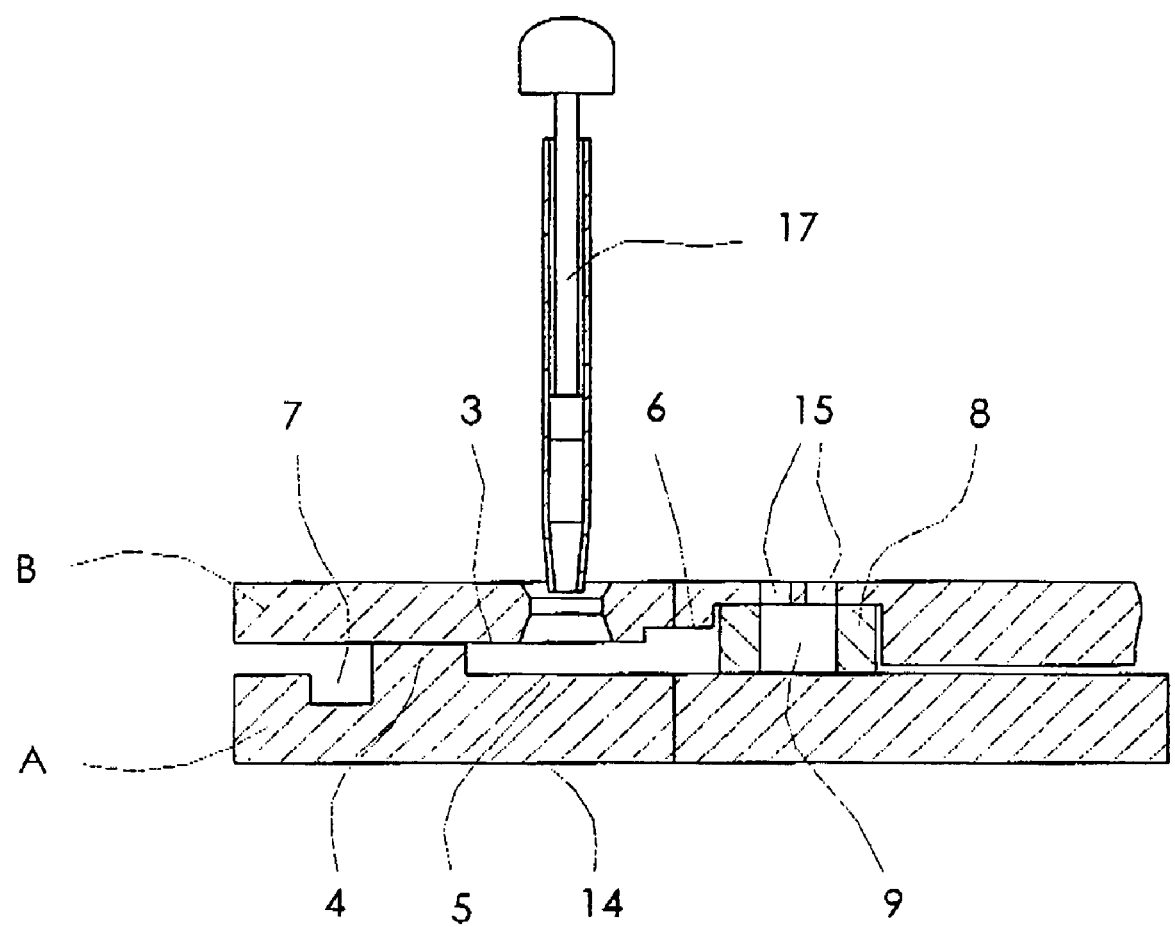

FIGS. 5A and 6A depict a slight modification of the embodiment shown in FIGS. 5 and 6 in respect of bore 16' form and position. The bore is here located in between the cavities 5,11, minimizing the flow distance for the liquid to reach the cavities. Furthermore, the bore is here given an elongated slit shape and positioned with the slit longer sides exposed towards the cavities, i.e. in the direction of the desired liquid flow.

Figure 7:
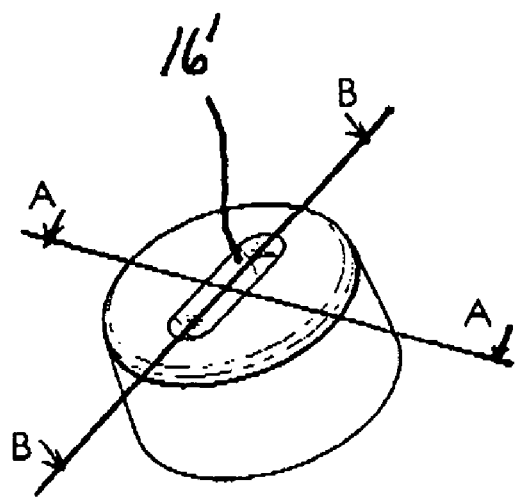
FIG. 7 shows the bore as an insert, in perspective view and in FIGS. 7A and 7B in sections transverse and along the long slit axis respectively.
Figure 7A:
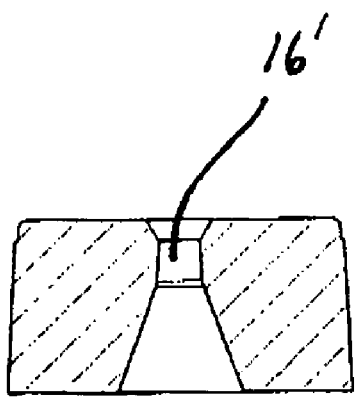
Figure 7B:
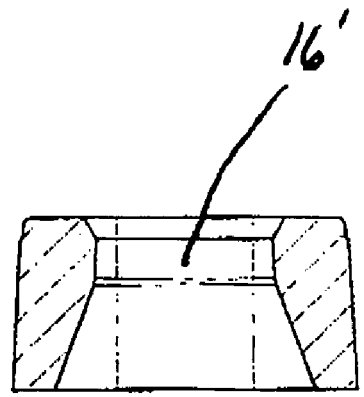

FIG. 7 shows the bore 16' as an insert, in perspective view and in FIGS. 7A and 7B in sections transverse and along the long slit axis respectively. Sample is intended to be provided from above, i.e. liquid flow is from above to below in the Figures. Sample can be provided either by a liquid drop placed directly on the slit or by an ejection instrument, e.g. the syringe 17, inserted into the bore upper part, and preferably then with a broad enough instrument tip to be stopped by the hour-glass narrowest section. As clearly seen in the cross-sections the bore 16' has the overall shape of an hour-glass with upper sides converging with a larger angle than the angle of the diverging lower sides. If the diverging angle is too large, or not diverging at all, liquid flow may not transfer properly into the channel below.

Moreover, in the embodiment shown in FIGS. 7, 7A, and 7B, respectively, the bore 16' has the shape of a elongated slit shaped funnel ending in the capillary channel, preferably having stopping devices against too deep penetration of the ejection instrument. In case of non-capillary feeding the bore 16' preferably has a narrowest flow area preferably being larger than that required for capillary feeding, thereby assist-ing in gravity filling, preferably, however, being noncircular, preferably slit-formed, for proper transition between non-capillary and capillary flow. For similar reasons the funnel preferably has a diverging portion after its narrowest part, giving an overall shape of an hour-glass, with a diverging outlet angle adapted for capillary flow.

Figure 8:
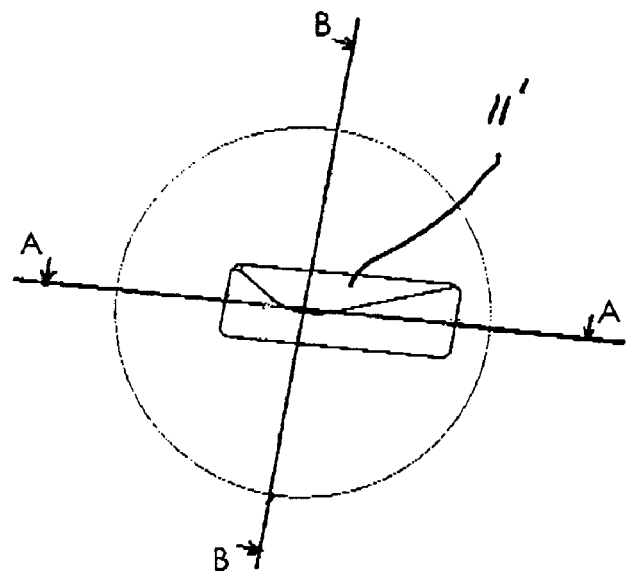
FIG. 8 shows a modified embodiment of larger cavity 11' in an illustrative side view, and in FIGS. 8a and 8B in sections along the long and short axes respectively.
Figure 8A:
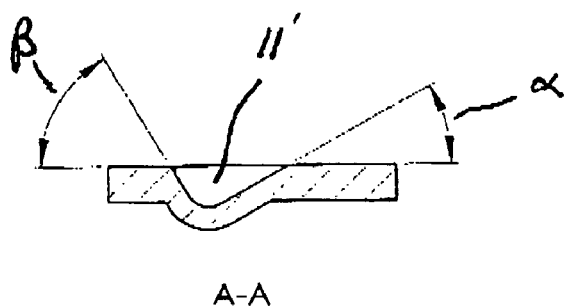
Figure 8B:
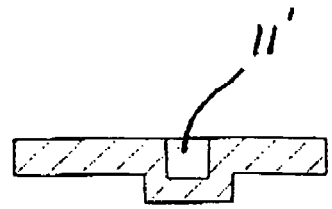
Figure 1:
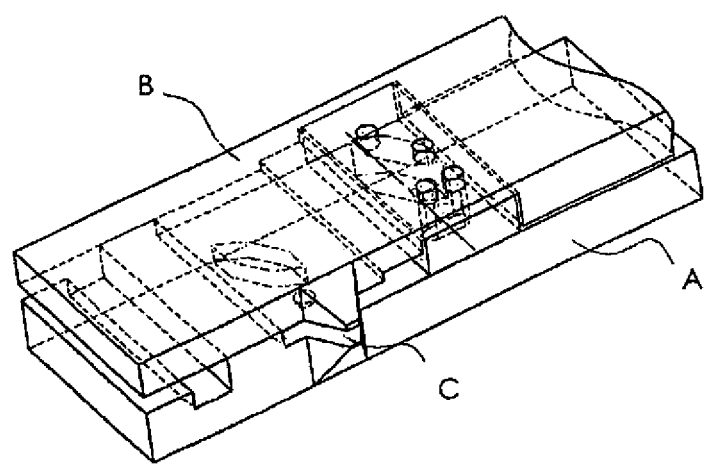
Figure 2:
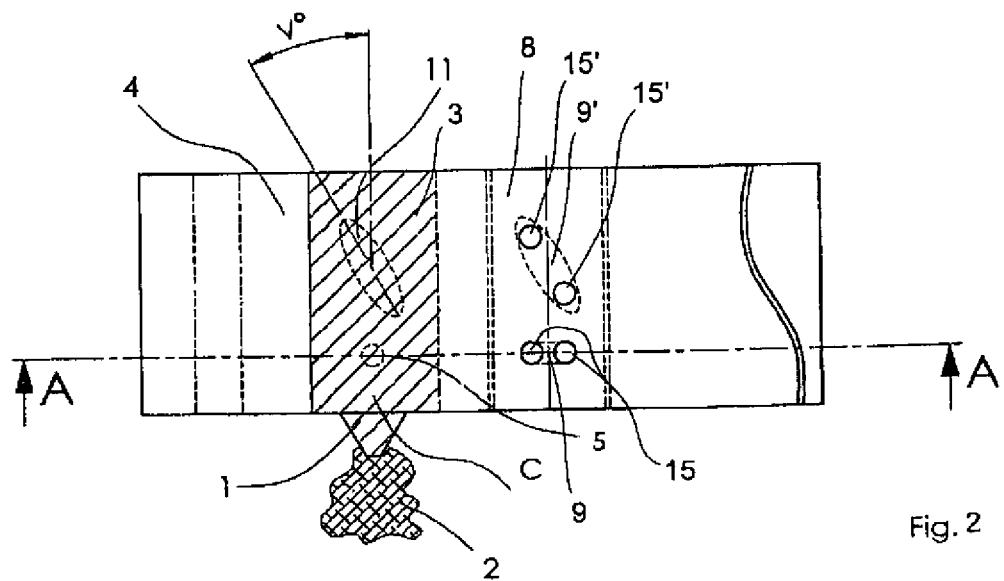
Figure 3:
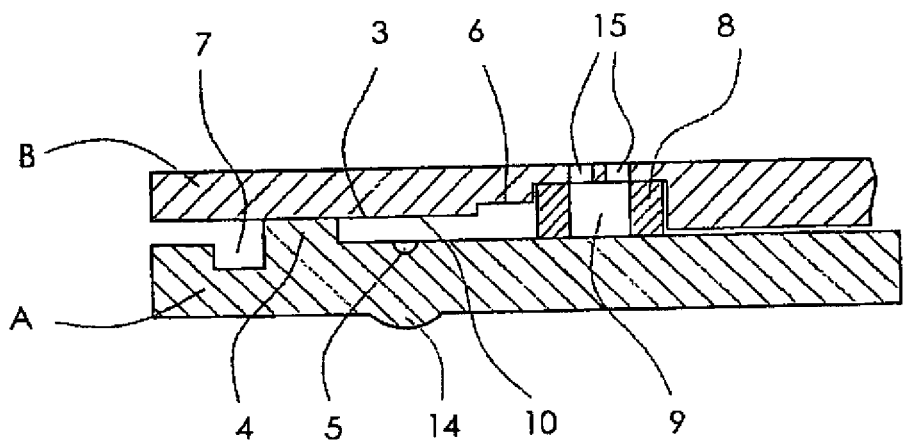
Figure 4:
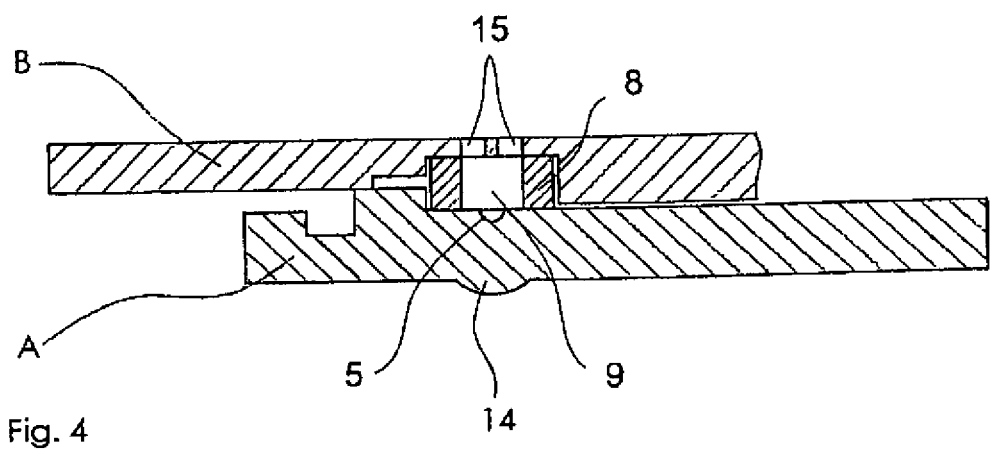
Figure 5:
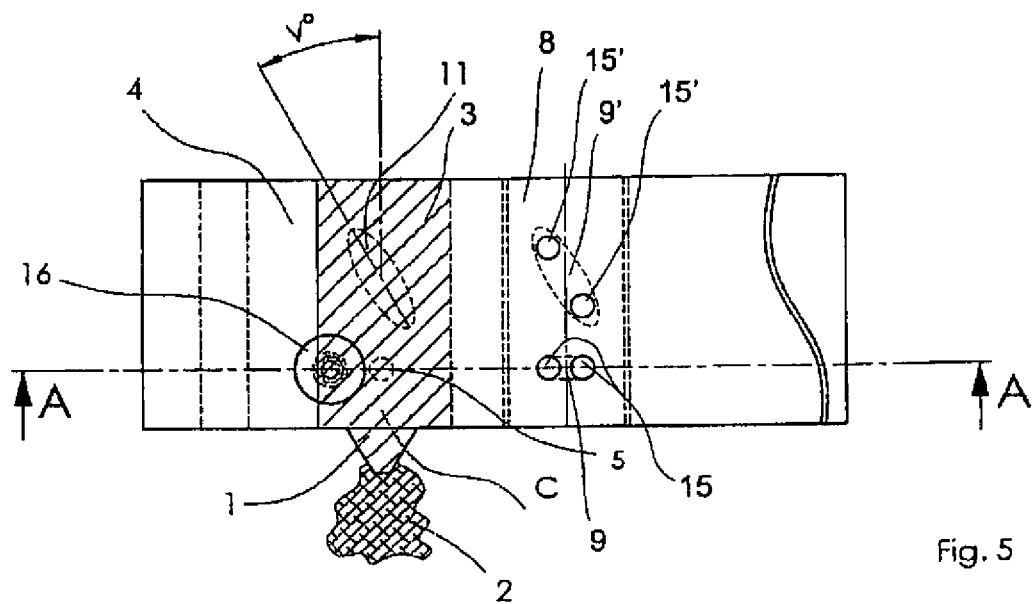
Figure 5A:
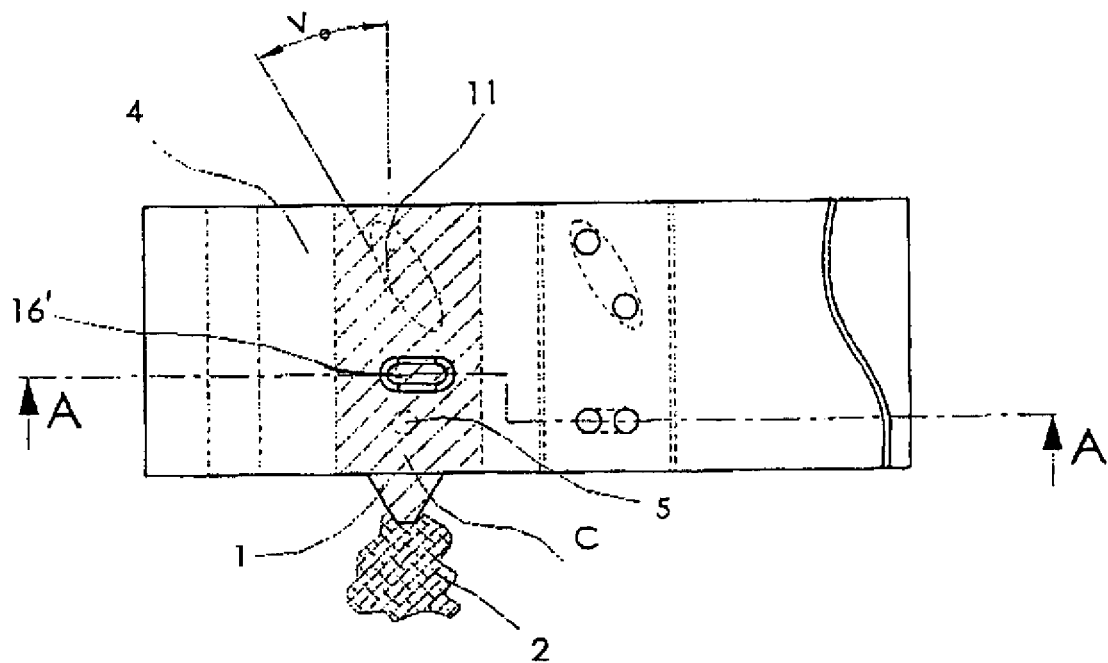
Figure 6:
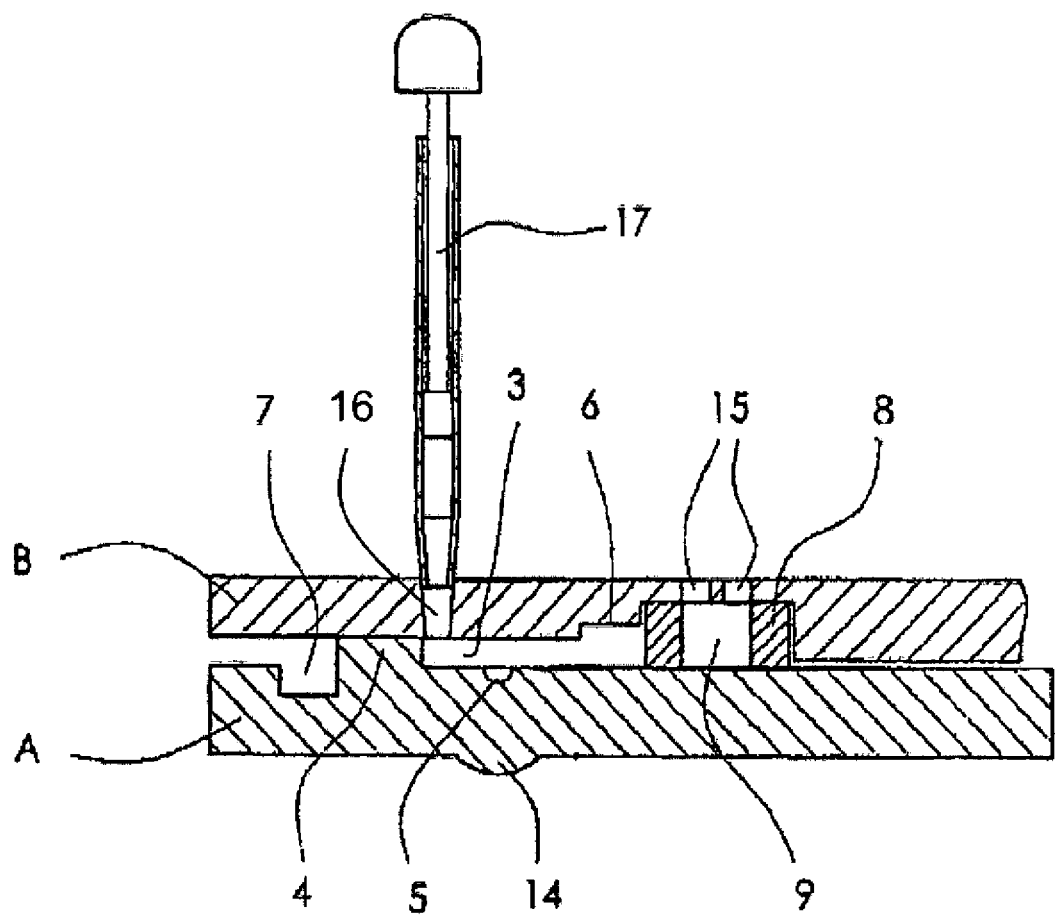
Figure 6A:
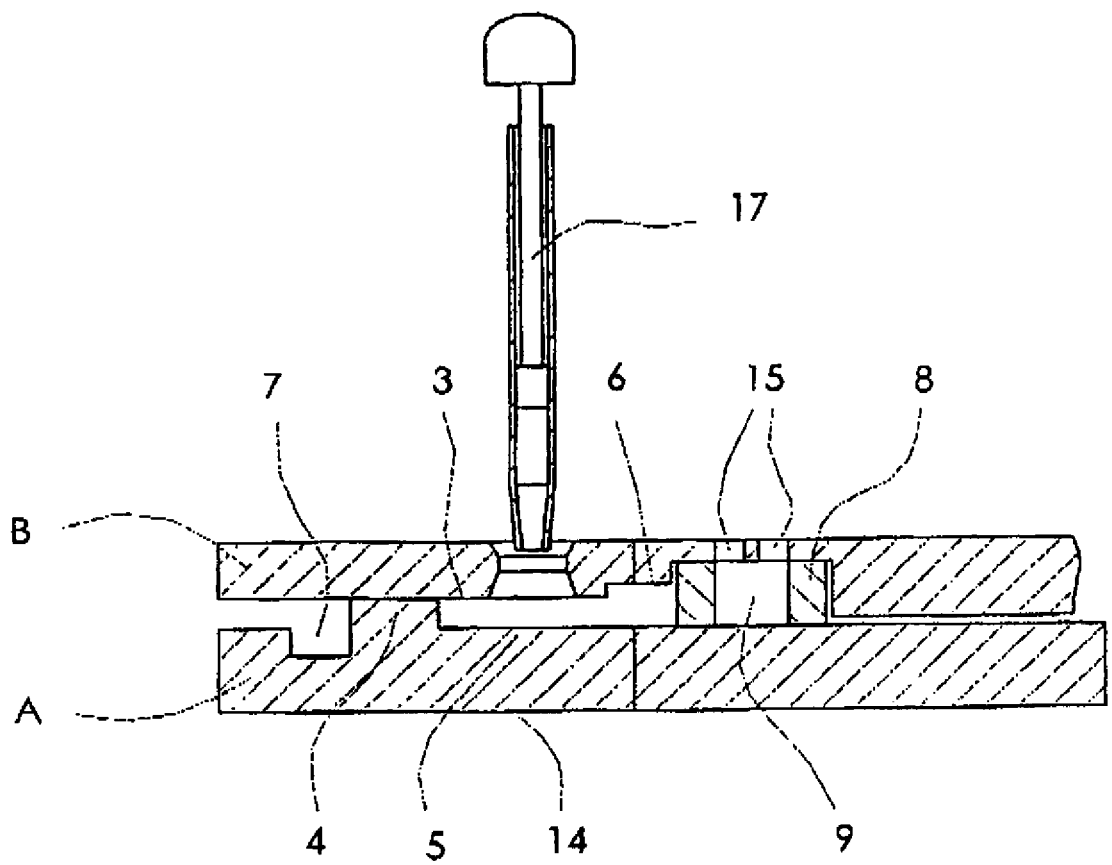
Figure 7:
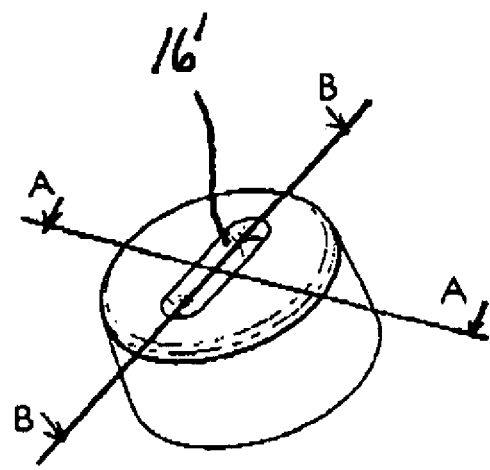
Figure 7A:
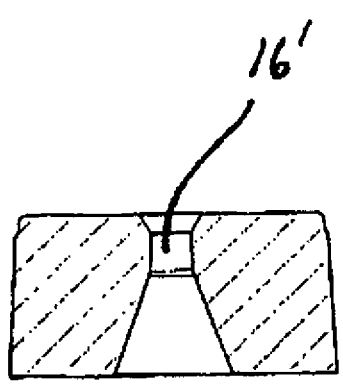
Figure 7B:
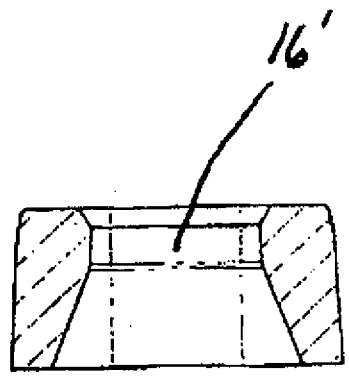
Figure 8:
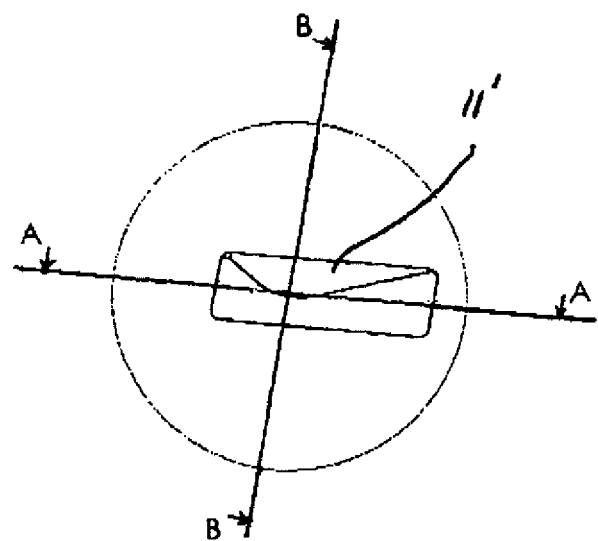
Figure 8A:
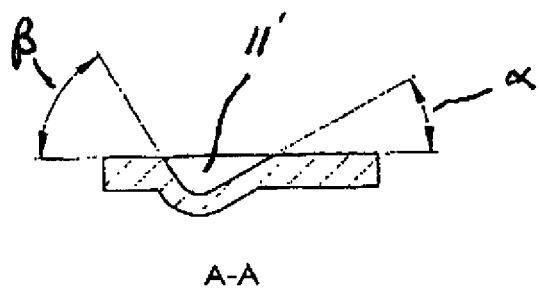
Figure 8B:
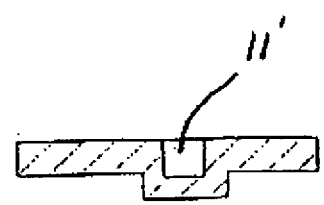

FIGS. 8, 8A, and 8*b* show a modified preferred embodiment of said at least one cavity 11' in which said at least one larger cavity 11' is designed for facilitated capillary filling. Said at least one larger cavity 11' is preferably shaped elongated, i.e. having an imaginary surface with a longer axis and a shorter axis perpendicular thereto, which gives an increased circumference to area ratio in relation to a circle, which elongated shape can take a variety of forms such as elliptical, rectangular etc. Preferably the cavity 11' has a general wedge like shape.

With reference to FIG. 8A, illustrating section A-A of FIG. 8, the liquid is intended to be fed from right and flow towards left in said Figure. As clearly seen in this section, at the right, up-flow, end the liquid flows into the cavity 11' along a more level slope, with a smaller angle α, than at the left, down-flow, end where the liquid flows out from the cavity 11' along a more steep slope, having a larger angle β.

As seen in FIG. 8B, illustrating section B-B of FIG. 8, the sides of the cavity 11' parallel with the intended liquid flow are steep, substantially with a 90° angle relative to the reference surface or channel 3.

The elongated form secures that the cavity 11' has an increase surface to volume ratio in relation to the minimal possible. Furthermore, the sides of cavity 11' substantially parallel to the flow direction are steep with respect to the reference surface.

It should be noted that the apparatus according to the second embodiment and the modified embodiments shown above also can be filled in the same way as the apparatus according to the first embodiment, i.e. the protrusion 1 is dipped down in the liquid sample 2, whereby the channel 3 and the cavities 5,11 and 11' are filled with the sample by capillary force. Thus, the syringe inlet through bore 16, 16' does not affect the capillary force in the channel.

The invention claimed is:

1. An apparatus for filling a sample volume defining device for separating at least one defined volume of a liquid sample from a relatively larger undefined volume of said sample, said device comprising:
   a) A first body and a second body movable relative to said first body, whereby said first body has at least one cavity in a surface thereof, said at least one cavity having a defined volume, and said second body includes a sealing and scraper means slidable along said surface and over said at least one cavity upon relative movement of said bodies whereby said accurately defined volume is achieved in said at least one cavity;
   b) A channel formed between said first and second bodies, disposed above and enclosing an area around said cavity on said upper surface of said first body, said channel having dimensions in width and length that facilitate capillary filling; and
   c) An inlet opening and a further opening to ambient air, both in fluid communication with said channel between said first and second bodies, said inlet opening adapted to fill a liquid sample therethrough into said channel, said cavity located between said inlet opening and said further opening to ambient air, said inlet opening positioned beyond said cavity at an up-flow direction with a distance along said upper surface of said first body from said cavity, and at the same time being in communication with said cavity through an enclosed space within said channel, said further opening to ambient air positioned at a down-flow direction of said cavity Wherein when said liquid sample is filled through said inlet opening into said channel, said liquid sample flows across said distance on said upper surface of said first body within said channel, with a wave front from said up-flow direction to said down-flow direction across said cavity, thereby said liquid sample fills said cavity in a manner than no air bubbles are entrapped in said cavity.

2. The device of claim 1, wherein said sealing and scraper means is made of a resilient material.

3. The device of claim 2, wherein said sealing and scraper means includes at least one aperture aligned with and in fluid communication with a pair of through-channels of said second body; and when said first body is slid, said cavity containing said defined volume of said liquid sample is then positioned in communication with said pair of through-channels of said second body through said aperture of said sealing and scraper means.

4. The device of claim 1, wherein said inlet opening is disposed through said second body, beyond said cavity on said upper surface of said first body, adapted to fill said liquid sample therethrough by injection.

5. The device of claim 1, wherein said channel between said first and second bodies is filled by gravity filling.

6. The device of claim 1, wherein a height of the channel is about 0.05-1.0 mm.

7. The device of claim 1, wherein said channel has a volume of about 20 to 40 microliter (µl).

8. The device of claim 1, wherein said cavity has a volume of less than 15 µl.

9. The device of claim 1, wherein said cavity has a volume of about 5 µl.

10. The device of claim 1, wherein a surface of said channel is coated with a material selected from the group consisting of dextran, proteins or derivatives thereof.

11. The device of claim 1, wherein at least a surface of said cavity is coated with a material selected from the group consisting of dextran, proteins or derivatives thereof.

12. The device of claim 11, wherein said surface of said cavity is coated with a material that gives a contact angle of 75°-0° between said liquid sample and a material forming the surface of said cavity.

13. The device of claim 1, wherein said cavity is elongated with a long axis and a short axis perpendicular thereto, and has a cross section along said long axis of a wedge like shape with a first end wall having a slow descending slope down to a bottom of said cavity; said cavity being orientated with said long axis in said up-flow direction, with said first end wall as an up-flow end and a second end wall as a down flow end of said cavity.

14. The device of claim 13, wherein said first and second end walls have different slopes and said second end wall has a steeper slope than said that of said first end wall.

15. The device of claim 14, wherein two sides of said cavity parallel to said long axis of said cavity have a steep slope.

16. The device of claim 1, wherein said first body is provided with a magnifying means in front of said cavity on a side opposing said upper surface.

17. The device of claim 1, wherein said first body further comprises a second cavity on said upper surface thereof, having a second defined volume different from that of said at least one cavity, said channel between said first and second bodies being above and enclosing an area around said second cavity and said inlet opening being beyond both of said cavities; wherein when said liquid sample is filled through said inlet opening into said channel, said liquid sample flows on said upper surface of said first body within said channel across said second cavity, with a wave front from an up-flow direction to a down-flow direction in reference to said second cavity, thereby said liquid sample fills said second cavity in a manner that no air bubbles are entrapped in said second cavity.

18. The device of claim 17, wherein when said first body is slid against said second body said sealing and scraper means scrapes said liquid sample above and around both of said cavities, obtaining two different defined volumes of said liquid sample in said cavities, respectively.

19. The device of claim 18, wherein said sealing and scraper means includes two apertures, each thereof aligned with and in fluid communication with one of two pairs of through-channels of said second body; and when said first body is slid, each of said cavities containing respective defined volume of said liquid sample is positioned in communication with said two pairs of through-channels of said second body through said apertures of said sealing and scraper means, respectively.

* * * * *

UNITED STATES PATENT AND TRADEMARK OFFICE
CERTIFICATE OF CORRECTION

PATENT NO. : 7,744,819 B2
APPLICATION NO. : 11/399423
DATED : June 29, 2010
INVENTOR(S) : Berndtsson et al.

It is certified that error appears in the above-identified patent and that said Letters Patent is hereby corrected as shown below:

Please delete patent 7,744,819 in its entirety and insert patent 7,744,819 in its entirety.

Signed and Sealed this
Eighteenth Day of December, 2012

David J. Kappos
*Director of the United States Patent and Trademark Office*

(12) United States Patent
Berndtsson et al.

(10) Patent No.: US 7,744,819 B2
(45) Date of Patent: Jun. 29, 2010

(54) APPARATUS FOR FILLING A SAMPLE VOLUME DEFINING DEVICE

(75) Inventors: Ingemar Berndtsson, Sollentuna (SE); Lennart Niklason, Sollentuna (SE)

(73) Assignee: Boule Medical AB, Stockholm (SE)

( * ) Notice: Subject to any disclaimer, the term of this patent is extended or adjusted under 35 U.S.C. 154(b) by 758 days.

(21) Appl. No.: 11/399,423

(22) Filed: Apr. 7, 2006

(65) Prior Publication Data
US 2006/0228263 A1    Oct. 12, 2006

(30) Foreign Application Priority Data
Apr. 8, 2005 (SE) .................................. 0500784

(51) Int. Cl.
*B01L 3/00* (2006.01)
*G01N 1/18* (2006.01)
(52) U.S. Cl. .......... 422/100; 73/863; 222/335; 222/399; 422/93; 422/103; 436/177; 436/180
(58) Field of Classification Search ................ 422/100
See application file for complete search history.

(56) References Cited

U.S. PATENT DOCUMENTS

| | | | | |
|---|---|---|---|---|
| 4,726,237 A | * | 2/1988 | Yung | 73/864.83 |
| 4,726,932 A | * | 2/1988 | Feier et al. | 422/103 |
| 4,896,546 A | * | 1/1990 | Cabrera et al. | 73/863.73 |
| 5,637,469 A | * | 6/1997 | Wilding et al. | 435/7.21 |
| 6,240,984 B1 | * | 6/2001 | Fawcett et al. | 141/130 |
| 6,872,361 B2 | * | 3/2005 | Li et al. | 422/103 |
| 2002/0172617 A1 | | 11/2002 | Biwa et al. | |
| 2003/0026741 A1 | | 2/2003 | Li et al. | |
| 2003/0099577 A1 | * | 5/2003 | Renaud et al. | 422/100 |
| 2005/0118061 A1 | | 6/2005 | Mototsu | |

FOREIGN PATENT DOCUMENTS

WO    WO-2005/052553 A1    6/2005

* cited by examiner

*Primary Examiner* — Krishnan S Menon
*Assistant Examiner* — Dirk Bass
(74) *Attorney, Agent, or Firm* — Latimer IP Law, LLP

(57) ABSTRACT

An apparatus for filling a sample volume defining device for separating at least one small defined volume of a liquid sample from a relatively larger undefined volume of said sample, said device including a first body and a second body movable relative to each other, whereby said first body has at least one cavity in a surface thereof, said at least one cavity having said defined volume. One of said first or said second body has at least one inlet opening adapted to be placed in a drop of the liquid sample. A defined channel is provided between said first and second body, which channel has fluid connection with said at least one opening and at least beyond said at least one cavity whereby the dimensions of said channel being such that said channel and said at least one cavity is filled with said liquid sample.

20 Claims, 8 Drawing Sheets

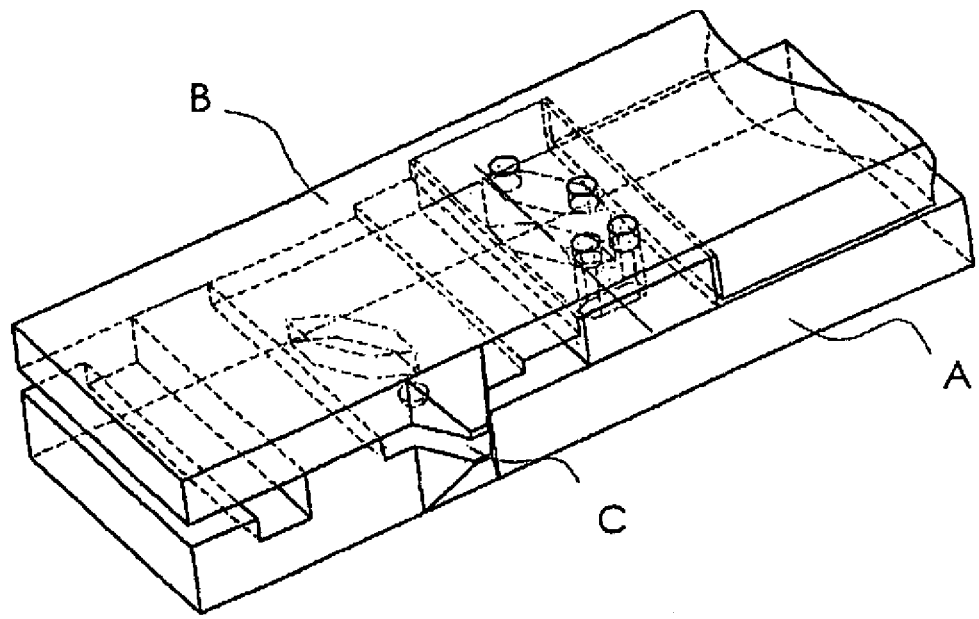

A - A

B - B

A-A

B-B

APPARATUS FOR FILLING A SAMPLE VOLUME DEFINING DEVICE

FIELD OF THE INVENTION

The present invention relates an apparatus for filling a sample volume defining device, particularly a disposable sample volume defining device, for separating at least one small defined volume of a liquid sample from a relatively larger undefined volume of said sample, said device including a first body and a second body movable relative to each other, whereby said first body has at least one cavity in a surface thereof, said at least one cavity having said defined volume, and said second body includes a means slidable along said surface and over said at least one cavity upon relative movement of said bodies, whereby said defined volume is achieved in said at least one cavity. The liquid sample is a blood sample, for instance.

BACKGROUND OF THE INVENTION

In blood testing, it is of crucial importance to define an accurate volume of a blood sample, since such accurately defined volume is later on used for certain tests. The accurately defined volume of blood sample is normally diluted by an accurately defined volume of a diluent or a lysing agent, in order to obtain a dilution of typically 1:100 to 1:80000. When counting white blood cells is concerned the dilution is typically 1:400 and when counting red blood cells (RBC) is concerned the dilution is typically 1:40000, in the latter case the dilution normally taking place in two steps. It is obvious, that measurement of sample volumes and dilution liquid volumes must be performed in an accurate and repeatable way such that a correct degree of dilution can always be guaranteed. Apparently, accurate measurement of sample volumes is a critical step in the dilution procedure, since the volumes concerned are extremely small compared to the corresponding diluent volumes.

To be able to obtain an accurate volume of a blood sample it is of crucial importance that the means in which the blood sample is contained is filled in a very precise and accurate and repeatable way.

A sample volume defining device of the above-identified type is known from the co-pending Swedish Patent Application No. 0303157-2. It has usually the form of a disposable cassette.

One problem when filling small cavities or voids or the like for obtaining the accurate and repeatable volume of a liquid sample, preferably a blood sample, is that the cavities are not filled in a proper way due to the formation of air bubbles in the cavities designed for the blood sample. Thus, there will be a difference in the volume between different blood samples and this will have a large significance when later counting the blood cells.

Another problem with known apparatus for testing of small volumes of a liquid sample/blood sample is to see when the apparatus is correctly filled.

Another problem is that the filling of known apparatus for testing of small volumes of a liquid sample/blood is dependent upon the direction of the apparatus when it is filled.

SUMMARY OF THE INVENTION

The object of present invention is to providing an apparatus for filling a sample volume defining device comprising at least two relatively movable bodies, one of which is provided with at least one cavity to be filled with liquid sample, for separating at least one accurately defined volume of a liquid sample from a relatively larger undefined volume of said sample.

A further object is to provide an apparatus of the above type in which it is easy to see when the cavity is filled with the liquid sample in an accurate and repeatable way.

A further object is to achieve an apparatus of the above type which is not dependent upon the filling direction.

Said object is achieved according to the present invention by an apparatus which is characterized in that that one of said first or said second body has at least inlet opening adapted to be connected with a drop of the liquid sample, that a defined channel is provided between said first and second body, which channel has fluid connection with said at least one inlet opening and at least beyond said at least one cavity, and that the dimensions of said channel being such that said channel and thereby said at least one cavity is filled with said liquid by capillary force.

As indicated a sample volume defining device is known from the co-pending application SE 0303157-2, incorporated by reference herein. Basically the volume defining process incorporates a) application of a relatively larger, often undefined, volume of the sample onto a surface and into a cavity formed in the surface and b) moving a scraping edge over the surface to leave a smaller defined volume of the sample in, the cavity. Further processing steps may follow, such as c) flushing the cavity with a liquid, such as a solution or reagent, to obtain a diluted sample, d) mixing the sample and diluent to obtain a homogenous diluted sample and e) performing measurements on the diluted and mixed sample.

For purposes of discussion the surface can be regarded as a reference surface, comprising the physical surface as well as an imaginary surface, flush and continuous with the physical surface, or defined in mechanical terms by movement of a thought entirely rigid scraper means in contact with the surface, across the cavity so as to define a target volume of the cavity limited by the imaginary surface. The reference surface shall at least surround the cavity to such an extent as to allow the scraping action and preferably the reference surface encircles the cavity on all sides.

The reference surface may have different shapes as long as it meets the continuity requirement, consistent with the scraping purpose. For example, the reference surface with its cavity may be double-curved, meaning that it cannot be formed by bending a flat surface, as exemplified with a cavity in a ball valve, or the reference surface may preferably be single-curved, meaning that it can be formed from a flat surface, as exemplified by a cavity in a cylinder valve, or most preferably it is substantially flat, as exemplified by a cavity in a slide valve.

The cavity size, i.e. the target volume under the imaginary surface, or rather the practical surface to be further discussed below, depends on several factors. Some of these factors are application dependent, such as sample nature and necessary volumes for planned dilution degrees or requirements for intended measurement. In disposable devices, for economical, reasons it is generally desirable to minimize the volumes in order also to minimize other features such as diluent volumes, mixing arrangements etc. However, manual manipulation and manufacturing constraints, e.g. molding of plastics, may place a lower limit to practical or possible cavity sizes. In case of several cavities, e.g. for different dilution degrees, the restrictions typically are set by the smallest cavity. General values are difficult to give but experience has indicated that the cavity volume should preferably be larger than 0.01 µl, preferably larger than 0.05 and most preferable larger than 0.1

µl. The maximum cavity volume can be kept below 50 µl, preferably below 25 µl and most preferably below 15 µl.

Similarly cavity shape may be determined by several factors. Besides manufacturing constraints that may put limits to advanced features of small cavities, desirable shape is mainly dictated by efficient filling and foreseeable, also expressed herein as reproducible, scraping results, of particular importance between different disposable devices.

Cavity filling may take place in various ways. As indicated, if a sample surplus is simply placed on the cavity there is a risk for gas inclusion and unfilled voids in the cavity. To avoid this the sample may be forced into the cavity, e.g. by a sample stream positively pumped by forced flow past the cavity, which, however, does not entirely secures flow through the cavity. Preferably then forced filling is made by insertion of a probe straight above or into the cavity, preferably with care taken against probe outlet contact and blocking, which cannot easily be compensated by increased injection pressure due to the hydraulic area relationship, and with necessary precision care needed for small cavities.

A preferred filling method is use of capillary forces for filling. It is believed that such filling takes place by wetting of liquid attraction surfaces highly independent of other forces applied to the liquid sample. Hence the criteria for capillary filling shall be regarded satisfied, and accordingly testable, if filling takes place, or can take place, without other forces applied. The criteria for filling without other forces applied is testable also in devices designed for application with other forces, e.g. syringe or gravity filling of sample into a channel designed for capillary filling. The non-presence of additional forces shall exclude forces needed to initiate capillary filling, which may require forced introduction of the liquid into a channel designed for capillary filling, e.g. forced wetting of a certain part of channel circumference for the capillary filling to continue autonomously. Capillary filling requires a certain surface to volume ratio to proceed, which ratio depends mainly on dimensions but also on among others on liquid to surface wetting attraction, the surface possibly being material selected or modified by plasma treatment, chemical modification, surface treatment etc., normally requiring a certain circumference length in relation to cross-section, which circumference need not be continuous but preferably forms a substantially closed channel. Capillary filling requirements are given by example herein, which requirements, however, should be determined for the actual materials and liquids involved.

Initiation of filling can be made in different ways. The supply can be made substantially along the reference surface, giving advantages in capillary wetting proceeding in the same direction as feeding. The supply can preferably be made from below, i.e. through the same structure that carries the cavity or cavities and with a flow substantially opposite to that needed for filling the cavity, e.g. for the purpose of avoiding interference with the structures introduced to stop capillary filling spreading laterally in the channel. The supply can most preferably be made from above the reference surface, e.g. for the purpose of the above proposes, for gravity assistance, for simplicity in the design and for the possibility of closing the feeding opening during the scraping arrangement movement.

The sample introduction site is preferably designed to assist in the above objects. Preferably the site is designed for compatibility with both direct sample introduction, e.g. a blood drop applied to the site, or device introduction for example by means of a syringe, a probe etc. A preferred design is a funnel ending in the capillary channel, preferably arranged for stopping devices against too deep penetration for reasons given, and most preferably having a narrowest flow area preferably being larger than that required for capillary feeding, thereby assisting in gravity filling, preferably, however, being noncircular, preferably slit-formed, for proper transition between non-capillary and capillary flow. For similar reasons the funnel preferably has a diverging portion after its narrowest part, giving an overall shape of an hour-glass, with a diverging outlet angle adapted for capillary flow for proceeding.

Common in the art are capillary tubes for aspiration of samples. The current cavities differs from such tubes in that the cavities extend from a reference surface, which reference surface in itself forms part of a sample filling channel in general, but preferably a filling channel designed for capillary filling, preferably lateral to cavity filling flow direction. The volume and shape of the filling channel are irrelevant as long as the cavity volume is well defined. The filling channel may comprise several cavities without major modifications of the reference surface carrying device. Filling of cavities arranged remote from, or at least not directly under, channel feeding structures avoids interference with any possible channel feeding device or probe as well as possible later flushing. Simplicity adds advantages over known valve type arrangements.

Without being bound by theory it is believed that capillary filling is driven by liquid affinity to surface and accordingly filling by this mechanism should be facilitated in general terms by a large surface to volume ratio. For a suitable capillary filling design, cavity size and shape come into play. Spherical shapes have the least surface to volume ratio. On the other hand small cavities generally have a larger surface to volume ratio than larger cavities, representing a further argument for minimization, a further merit of the present invention to have realized. Accordingly shape is less important for small cavities where even forms close to spherical or partially spherical can be accepted, whereas larger cavities with preference are given a shape with higher than, partial or full, spherical surface to volume ratio, e.g. tube or channel forms. The distinction between "smaller" and "larger" respectively can herein roughly be understood as cavities having depths "shallower" and "deeper" respectively than double the minimum required for capillary flow to proceed in a continuous channel of that dimension. The reason the cavities can be deeper than the capillary minimum is believed to be that the channel, of capillary dimensions, provides a river of liquid drag that locally, i.e. at the cavities, can overwhelm larger dimensions locally.

Due to the surface wetting theory, it is further believed that sharp edges are easily traversed by a capillary driven liquid front if the edge is concave, i.e. a surface angle in the intersection of less than 180°, as seen from the wet side, whereas convex edges, i.e. a surface angle in the intersection of more than 180°, are less easily traversed. Accordingly it is preferred that that at least the convex edges are smoothed out to facilitate capillary flow transfer by reducing the angle. This preferably applies to the arrival direction of the capillary flow front, i.e. the up-flow end, whereas the other end, i.e. down-flow end, is regarded less critical.

In summary, at least larger cavities should be designed for facilitated capillary filling. Smaller cavities are less critical and, furthermore, common manufacturing methods such as plastic moulding normally result in smoothed out transition surfaces, beneficial for capillary filling. At least the larger cavities are preferably shaped elongated, i.e. having an imaginary surface with a longer axis and a shorter axis perpendicular thereto, which gives an increased circumference to area ratio in relation to a circle, which elongated shape can take a variety of forms such as elliptical, rectangular etc. In case of more complicated forms these can be compared with elliptical shape of the same area for determination of the longer and shorter axes. Preferably such a cavity is located with at least a vector component and preferably its full long axis parallel with the capillary filling flow direction, i.e. with respect to the arriving capillary liquid front, herein referred to as the up-flow direction. The elongated form secures that the cavity has an increase surface to volume ratio in relation to the minimal possible. It is further preferred that the cavity up-flow end has a slow descending slope down into the cavity, as seen in the liquid flow direction, and furthermore that the cavity sides substantially parallel to the flow direction are steep with respect to the reference surface.

The cavity may have several openings, or entrances, e.g. the cavity may form a tube extending between two openings as in known capillary tubes although here also connecting to a capillary driven filling channel. It is preferred, however, that to the extent the channel has more than one opening these opens into one and the same reference surface. Most preferably the cavity has only one opening for best filling and scraping properties.

A sloping arrangement is consistent with a cavity design narrowing away from the reference surface and, in case of cavities with only one opening, towards its bottom or, differently expressed, that cross-sections taken parallel with the reference surface have decreasing cavity areas when moving away from the reference surface, at least over a part of the cavity depth and preferably over substantially the cavity full depth. It is further preferred that the cavity walls are at least substantially perpendicular but preferably converging towards the cavity bottom, the bottom being the end farthest away form the reference surface. Most preferably small or no undercut parts are present in the cavity.

Filling of the cavity or cavities is facilitated if the cavity is designed assist in capillary filling, meaning that cavity surface to volume ratio, at least in the sample flow direction, meets the capillary filling requirement. If the channel has sufficiently strong surface affinity the cavity surfaces may exceed the surface to volume relationship for capillary filling but preferably the cavity dimensions lies within that of the capillary filling requirements, disregarding here the additional dimensions provided by the channel.

Discussing next the scraping, the imaginary surface has been described above as an idealized surface entirely continuous with the reference surface. However, in practice any scraping device able to be kept in good contact with the reference surface must have a certain resilience, preferably the minimum resilience necessary for dynamic adaptation to the reference surface, which is preferably made of a harder material, without undue further deformation. Certainly the material in the scraping device should not be soft, in the sense that it easily deforms permanently. Suitable materials may include thermoplastics and preferably eleastomerics. The scraper resilience means that it will expand by deflection to a certain extent into the cavity volume, thereby creating an actual, or practical, opening surface for the cavity, generally so as to reduce the cavity volume somewhat. This may not be a problem as long as the reduction is predictable and foreseeable. In order to facilitate such predictability it may be of interest to minimize the volume deviation between the imaginary and practical surfaces.

Although the scraping device can expand into the cavity both in the scraping direction and in directions perpendicular thereto, if it in the preferred way has a sufficient length in the scraping direction for coverage of the entire cavity, it is believed that the deviation is reduced if it is elongated as described, i.e. with a shorter axis as well as a longer axis.

In at least on one sense scraping is asymmetrical, namely when the scraping edge enters over the cavity opening, where deflection starts, and even more when the edge leaves the cavity opening, where full deflection must decrease, the latter being deemed more important than the former. In order to minimize influence of at least the latter effect it is preferred to reduce cavity opening size lateral to the scraping direction in relation to the opening size parallel to the scraping direction, consistent with an elongated form as discussed. It is further preferred to avoid linear contact between the scraper edge and at least the cavity edge when entering or at least when leaving the cavity opening, meaning that point contact is preferred during at least leaving. This can be achieved by making the scraping edge non-congruent with the cavity opening leaving edge, e.g. by having a linear scraping edge and a bent cavity opening leaving edge or vice versa, in the latter case preferably by a concave scraping edge in order to lift the peripheral scraping edges prior to lifting its central parts when passing the cavity opening leaving edge. Alternatively the scraper edge can meet an elongated cavity opening at an angle with respect to cavity opening longer axis.

In summary, in order to strike a balance between the cavity shape design dictated by filling and the design dictated by scraping, it is preferred that the cavity has an elongated opening surface and that the filling direction and the scraping direction have at least a vector component in common, preferably a longer vector component in common and most preferably are substantially parallel. It is further preferred that at least the up-flow, and scraping entrance, cavity end wall has a slow slope whereas other cavity wall are steeper.

As indicated, all these observations applies more to larger cavities than to smaller cavities.

BRIEF DESCRIPTION OF THE INVENTION

A non-limiting example of the present inventions will be described hereinafter with reference to the accompanying drawings, wherein:

FIG. 1 is a schematic partial perspective view showing the apparatus according to a first embodiment of the invention in which hidden parts and two cavities are shown in phantom lines.

FIG. 2 is a partial view from above of the apparatus according to a first embodiment shown in FIG. 1 in which hidden parts and two cavities are shown in phantom lines, together with a liquid sample to be tested.

FIG. 3 is a partial sectional side view of the apparatus according to a first embodiment take along the line A-A in FIG. 2.

FIG. 4 is a partial sectional side view of the apparatus according to a first embodiment taken along the line A-A in FIG. 2 with the two bodies A, B moved relatively to each other.

FIG. 5 is a partial view from above of the apparatus according to a second embodiment provided with an syringe inlet through bore and in which hidden parts and two cavities are shown in phantom lines, together with a liquid sample to be tested.

FIG. 6 is a partial sectional side view of the apparatus according to a second embodiment taken along the line A-A in FIG. 5 provided with a syringe.

FIGS. 5A and 6A depict a slight modification of the embodiment of FIGS. 5 and 6 in respect of bore 16' form and position.

FIG. 7 shows the bore as an insert, in perspective view and in FIGS. 7A and 7B in sections transverse and along the long slit axis respectively.

FIG. 8 shows a modified embodiment of larger cavity 11' in an illustrative side view, and in FIGS. 8a and 8B in sections along the long and short axes respectively.

DESCRIPTION OF PREFERRED EMBODIMENTS

In FIG. 1 the apparatus according to a first embodiment comprises two bodies, i.e. a first body comprising a sledge A and a second body comprising a framework B, movable relatively to each other and in close contact. The apparatus forms a part of a disposable support (not shown), preferably in the form of a cassette, and the framework B is formed integrally with said support. The support comprises at least two chambers, one of which is filled with an accurately defined volume of diluent or lysing agent for dilution of a liquid sample, preferably a blood sample, and the other is used for achieving the dilution and mixing of the liquid sample.

The sledge A or the framework B or both are provided with suitable interengaging means (not shown) so that they can move relative to each other in close contact.

As can be seen from FIG. 3, between the sledge A and the framework B is a defined channel 3 arranged and provided with at least one inlet opening C for a liquid sample 2 (FIG. 2). To facilitate the filling of the channel the inlet opening C has in a preferred embodiment a protrusion 1.

The channel 3 has fluid connection with and extends as an elongation of said at least one inlet opening and beyond at least one accurately defined cavity 5. The accurately defined cavity 5 is made in the sledge A and aligned with said channel 3.

One aspect of the invention is to fill said at least one cavity 5 with the blood sample in an accurate and repeatable way. The inventors have found this is best done by capillary force. While not wishing to be bounded by a particular theory, the inventors believe that, by using capillary force, the liquid sample forms a wave front in the channel which fills said defined channel 3 and said at least one cavity 5 in such a way that no air bubbles are entrapped in the cavity 5.

By using capillary force for filling, a further aspect of the invention is achieved in that the accurate filling of said at least one cavity 5 is made independent of the direction for filling the apparatus of the disposable support, whereby the disposable support can be handled in a much easier way by, for instance, a nurse.

For enabling capillary force to be developed, the defined channel, formed in either the sledge A or the framework B or between the sledge and the framework, has a particularly chosen form, and the distance between the framework and the sledge, i.e. the height of the channel, is between 0.05-1.0 mm, preferably 0.1-0.3 mm, and most preferably 0.2 mm.

Below is given an example of how the defined channel can be designed, but the invention should not be regarded as limited to said design. Instead, the inventive conception is that the defined channel is filled with the liquid sample by capillary force.

In the embodiment shown in the FIGS. 1 and 2 two accurately defined cavities 5, 11 are formed in the sledge. As an example the larger cavity 11 has a volume of about 5 µl and the smaller cavity 5 about 0.1 µl, and the volume of the channel 3 is about 20-40 µl. However, to simplify the description of the invention said cavities are described as at least one cavity 5,11.

Thus, according to one aspect of the invention the defined channel 3 has the shape of a rectangle in cross section and is formed between the sledge A and the framework B, and one of the long sides of the channel 3 is delimited by a rim 4 formed on the sledge A and the other long side by a recess 6 formed in the framework B. One of the short sides of the channel 3 forms the inlet opening C and the other short side is open to the ambient air.

The rim 4 has close contact with the framework B, and on the long side of the rim opposite to the channel 3 (to the left as seen in FIG. 3) a recess 7 is arranged which stops the liquid sample from further spreading due to the fact that the distance between the sledge and the framework is too large for a capillary force to be developed. In a similar way, the recess 6 also stops the liquid sample from further spreading. Thus, only the channel will be filled with the liquid sample and this is shown in FIG. 2 with dashed lines. However, the physical means that delimit the channel 3 and recess 6 to the right side, as seen in FIG. 3, is a sealing and scraper means 8.

In principle, the design of the defined channel 3 can be made in many ways but according to the invention, it is important that the capillary force is stopped by some type of barrier means so that only the defined channel is filled with the liquid sample.

The sledge A is preferably made of a transparent material so that it is easily seen when the channel and thereby said at least one cavity 5,11 is accurately filled with the liquid sample, and in the case of a blood sample the defined channel will be seen red.

To further increase the control that said at least one cavity 5,11 is accurately filled with the liquid sample the sledge A may be provided with a magnifying means 14, for instance a magnifying glass, which is made in front of said at least one cavity 5,11, as seen in FIG. 3.

As seen in FIG. 3, for instance, the framework B is provided also with the sealing and scraper means 8 made of nitrile rubber. The sealing and scraper means 8 has at least one aperture 9 or 9' aligned with channels 15 or 15' provided in the framework B and in fluid communication with the at least two chambers in the support (not shown).

In case of blood testing, the channel 3 is filled with blood by capillary force and when the accurately defined volume of blood is to be achieved and diluted by the accurately defined volume of diluent or lysing agent, the sledge A is moved relative to the framework B, as seen in FIG. 4, so that the sealing and scraper means 8 scrapes off the excess of blood in the channel 3, whereby an accurately defined volume of blood is attained in said at least one cavity 5,11. When the sledge A and the framework are moved relative to each other the rim 4 acts as a pusher means for the blood in the channel 3 so that, under no circumstances, the volume of the blood sample in cavities 5,11 will be changed. Said at least one cavity 5,11 is brought also in fluid communication with the channels 15, 15 ', respectively through the aperture 9, 9', respectively, in the sealing and scraper means 8 and thus the diluent or lysing agent containing chambers. The accurately defined volume of blood is then mixed with the accurately defined volume of diluent or lysing agent and thereafter the blood cells are counted.

In a first embodiment according to the invention said at least one cavity 11 has the shape of an elliptical cavity, as seen from above in FIG. 2, and the major axis of the elliptical cavity preferably makes an angle V with the longitudinal direction of the channel 3 of about 20-60°. The object of arranging the cavity 11 with said angle is to minimize the risk that, when the sledge A and thereby the cavity 11 is moved relative the framework B, the leading edge of the sealing and scraper means 8, which moves over the cavity, expand into the cavity due to the fact that said means is made of a resilient material. If this happens the accurately defined volume of the liquid sample in the cavity will change in an unfavourable way. The cavity 11 having a relatively large volume (about 5 µl) and the cavity 5 having a relatively smaller volume (about 0.1 µl) are filled by the wave front of the liquid sample filling the channel 3 without any air bubbles being formed in said cavities. The smaller cavity 5 can have the form of a half-sphere.

The filling of channel 3 with the liquid sample can be improved if the surfaces enclosing said channel are made of or coated with a material selected from the group consisting of dextran, proteins or derivatives thereof or other means or materials known by the artisan that give a contact angle of 75°-0°, preferably 50°-0°, between the blood and the material forming the surfaces. It may be enough that only the surface of said at least one cavity 5,11 is coated with the above-mentioned material.

In FIGS. 5 and 6 a second embodiment of the apparatus according to the invention is shown. The first and the second embodiments of the apparatus according to the invention are made and work in exactly the same way with the exception of that, in the second embodiment, one of the sledge A or the framework B, preferably the framework B, is provided with a syringe inlet through bore 16 which opens in the channel 3, preferably close to rim 4 (see FIG. 6), and in which a syringe 17, preferably a capillary dispenser commercially available from Drummond Scientific Co., the United States, is adapted to be inserted. The channel 3 is thus filled with the liquid sample by a combination of capillary force and injection when said sample is injected and thereby the cavity 5,11 is filled. Thus, the at least one cavity 5,11 is filled in an accurate and repeatable way as in the first embodiment.

Preferably, the volume of the syringe is adapted to the volume of the channel 3 so that the channel 3 is not filled too much when the liquid sample is injected, whereby losses of liquid sample can be avoided.

An advantage when using a syringe for filling the channel 3 is that the liquid sample to be tested can be drawn from a test tube or from any other means, especially in veterinary applications.

FIGS. 5A and 6A depict a slight modification of the embodiment shown in FIGS. 5 and 6 in respect of bore 16' form and position. The bore is here located in between the cavities 5,11, minimizing the flow distance for the liquid to reach the cavities. Furthermore, the bore is here given an elongated slit shape and positioned with the slit longer sides exposed towards the cavities, i.e. in the direction of the desired liquid flow.

FIG. 7 shows the bore 16' as an insert, in perspective view and in FIGS. 7A and 7B in sections transverse and along the long slit axis respectively. Sample is intended to be provided from above, i.e. liquid flow is from above to below in the Figures. Sample can be provided either by a liquid drop placed directly on the slit or by an ejection instrument, e.g. the syringe 17, inserted into the bore upper part, and preferably then with a broad enough instrument tip to be stopped by the hour-glass narrowest section. As clearly seen in the cross-sections the bore 16' has the overall shape of an hour-glass with upper sides converging with a larger angle than the angle of the diverging lower sides. If the diverging angle is too large, or not diverging at all, liquid flow may not transfer properly into the channel below.

Moreover, in the embodiment shown in FIGS. 7, 7A and 7B, respectively, the bore 16' has the shape of a elongated slit shaped funnel ending in the capillary channel, preferably having stopping devices against too deep penetration of the ejection instrument. In case of non-capillary feeding the bore 16' preferably has a narrowest flow area preferably being larger than that required for capillary feeding, thereby assisting in gravity filling, preferably, however, being noncircular, preferably slit-formed, for proper transition between non-capillary and capillary flow. For similar reasons the funnel preferably has a diverging portion after its narrowest part, giving an overall shape of an hour-glass, with a diverging outlet angle adapted for capillary flow.

FIGS. 8, 8A, and 8b show a modified preferred embodiment of said at least one cavity 11' in which said at least one larger cavity 11' is designed for facilitated capillary filling. Said at least one larger cavity 11' is preferably shaped elongated, i.e. having an imaginary surface with a longer axis and a shorter axis perpendicular thereto, which gives an increased circumference to area ratio in relation to a circle, which elongated shape can take a variety of forms such as elliptical, rectangular etc. Preferably the cavity 11' has a general wedge like shape.

With reference to FIG. 8A, illustrating section A-A of FIG. 8, the liquid is intended to be fed from right and flow towards left in said Figure. As clearly seen in this section, at the right, up-flow, end the liquid flows into the cavity 11' along a more level slope, with a smaller angle $\alpha$, than at the left, down-flow, end where the liquid flows out from the cavity 11' along a more steep slope, having a larger angle $\beta$.

As seen in FIG. 8B, illustrating section B-B of FIG. 8, the sides of the cavity 11' parallel with the intended liquid flow are steep, substantially with a 90° angle relative to the reference surface or channel 3.

The elongated form secures that the cavity 11' has an increase surface to volume ratio in relation to the minimal possible. Furthermore, the sides of cavity 11' substantially parallel to the flow direction are steep with respect to the reference surface.

It should be noted that the apparatus according to the second embodiment and the modified embodiments shown above also can be filled in the same way as the apparatus according to the first embodiment, i.e. the protrusion 1 is dipped down in the liquid sample 2, whereby the channel 3 and the cavities 5,11 and 11' are filled with the sample by capillary force. Thus, the syringe inlet through bore 16, 16' does not affect the capillary force in the channel.

The invention claimed is:

1. An apparatus for filling a sample volume defining device for separating at least one defined volume of a liquid sample from a relatively larger undefined volume of said sample, said device comprising:

a first body and a second body movable relative to each other; said first body having at least one cavity having a defined volume in a form of a recess on an upper surface of said first body, said second body including a sealing and scraper means slidable along said upper surface and over said at least one cavity of said first body upon relative movement of said bodies;

a channel formed between said first and second bodies, disposed above and enclosing an area around said cavity on said upper surface of said first body; said channel having larger width and length than those of said cavity, at least one dimension of said channel facilitating capillary filling; and an inlet opening and a further opening to ambient air, both in communication with said channel between said first and second bodies, with said inlet opening adapted to fill a liquid sample therethrough into said channel; said cavity located between said inlet opening and said further opening to ambient air, said inlet opening positioned beyond said cavity at an up-flow direction with a distance along said upper surface of said first body from said cavity, and at the same time being in communication with said cavity through an enclosed space within said channel; said further opening to ambient air positioned at a down-flow direction of said cavity;

wherein when said liquid sample is filled through said inlet opening into said channel, said liquid sample flows across said distance on said upper surface of said first body within said channel, with a wave front from said up-flow direction to said down-flow direction across said cavity, whereby said liquid sample fills said cavity in a manner that no air bubbles are entrapped in said cavity, and wherein when said first body is slid against said second body, said sealing and scraper means scrapes said liquid sample above and around said cavity, obtaining said defined volume of said liquid sample in said cavity.

2. The device of claim 1, wherein said sealing and scraper means is made of a resilient material.

3. The device of claim 2, wherein said sealing and scraper means includes at least one aperture aligned with and in fluid communication with a pair of through-channels of said second body; and when said first body is slid, said cavity containing said defined volume of said liquid sample is then positioned in communication with said pair of through-channels of said second body through said aperture of said sealing and scraper means.

4. The device of claim 1, wherein said inlet opening is disposed through said second body, beyond said cavity on said upper surface of said first body, adapted to fill said liquid sample therethrough by injection.

5. The device of claim 1, wherein said channel between said first and second bodies is filled by gravity filling.

6. The device of claim 1, wherein a height of the channel is about 0.05-1.0 mm.

7. The device of claim 1, wherein said channel has a volume of about 20 to 40 microliter ($\mu$l).

8. The device of claim 1, wherein said cavity has a volume of less than 15 $\mu$l.

9. The device of claim 1, wherein said cavity has a volume of about 5 $\mu$l.

10. The device of claim 1, wherein a surface of said channel is coated with a material selected from the group consisting of dextran, proteins or derivatives thereof.

11. The device of claim 1, wherein at least a surface of said cavity is coated with a material selected from the group consisting of dextran, proteins or derivatives thereof.

12. The device of claim 11, wherein said surface of said cavity is coated with a material that gives a contact angle of 75°-0° between said liquid sample and a material forming the surface of said cavity.

13. The device of claim 1, wherein said cavity is elongated with a long axis and a short axis perpendicular thereto, and has a cross section along said long axis of a wedge like shape with a first end wall having a slow descending slope down to a bottom of said cavity; said cavity being orientated with said long axis in said up-flow direction, with said first end wall as an up-flow end and a second end wall as a down flow end of said cavity.

14. The device of claim 13, wherein said first and second end walls have different slopes and said second end wall has a steeper slope than that of said first end wall.

15. The device of claim 14, wherein two sides of said cavity parallel to said long axis of said cavity have a steep slope.

16. The device of claim 1, wherein said first body is provided with a magnifying means in front of said cavity on a side opposing said upper surface.

17. The device of claim 1, wherein said first body further comprises a second cavity on said upper surface thereof, having a second defined volume different from that of said at least one cavity, said channel between said first and second bodies being above and enclosing an area around said second cavity and said inlet opening being beyond both of said cavities; wherein when said liquid sample is filled through said inlet opening into said channel, said liquid sample flows on said upper surface of said first body within said channel across said second cavity, with a wave front from an up-flow direction to a down-flow direction in reference to said second cavity, thereby said liquid sample fills said second cavity in a manner that no air bubbles are entrapped in said second cavity.

18. The device of claim 17, wherein when said first body is slid against said second body said sealing and scraper means scrapes said liquid sample above and around both of said cavities, obtaining two different defined volumes of said liquid sample in said cavities, respectively.

19. The device of claim 18, wherein said sealing and scraper means includes two apertures, each thereof aligned with and in fluid communication with one of two pairs of through-channels of said second body; and when said first body is slid, each of said cavities containing respective defined volume of said liquid sample is positioned in communication with said two pairs of through-channels of said second body through said apertures of said sealing and scraper means, respectively.

20. The device of claim 1, wherein the height dimension of said channel facilitates capillary filling.

* * * * *